US012605216B2

(12) United States Patent     (10) Patent No.: US 12,605,216 B2
Gusein et al.     (45) Date of Patent: Apr. 21, 2026

(54) MEDICAL INSTRUMENT WITH ROTARY END EFFECTOR, POSITION SENSOR, AND ELECTROMAGNETIC INTERFERENCE REDUCTION

(71) Applicant: Acclarent, Inc., Irvine, CA (US)

(72) Inventors: George Gusein, Acre (IL); Tamir Yellin, Yokneam Moshava (IL); Hao H. Tran, Santa Ana, CA (US); Alex Gonzalez, Lake Forest, CA (US); Nitin P. Wale, Santa Barbara, CA (US)

(73) Assignee: Acclarent, Inc., Irvine, CA (US)

( * ) Notice: Subject to any disclaimer, the term of this patent is extended or adjusted under 35 U.S.C. 154(b) by 239 days.

(21) Appl. No.: 18/594,195

(22) Filed: Mar. 4, 2024

(65) Prior Publication Data

US 2024/0366313 A1     Nov. 7, 2024

Related U.S. Application Data

(60) Provisional application No. 63/464,264, filed on May 5, 2023.

(51) Int. Cl.
| | |
|---|---|
| *A61B 34/20* | (2016.01) |
| *A61B 17/00* | (2006.01) |
| *A61B 17/32* | (2006.01) |

(52) U.S. Cl.
CPC ........ *A61B 34/20* (2016.02); *A61B 17/00234* (2013.01); *A61B 17/32002* (2013.01); *A61B 2034/2051* (2016.02)

(58) Field of Classification Search
CPC ........ A61B 17/00234; A61B 17/32002; A61B 2034/2051; A61B 34/20
See application file for complete search history.

(56) References Cited

U.S. PATENT DOCUMENTS

| | | | |
|---|---|---|---|
| 3,722,505 | A | 3/1973 | Kolin |
| 7,720,521 | B2 | 5/2010 | Chang et al. |
| 9,459,087 | B2 | 10/2016 | Dunbar et al. |
| 9,554,812 | B2 | 1/2017 | Inkpen et al. |
| 10,463,242 | B2 | 11/2019 | Kesten et al. |
| 10,561,370 | B2 | 2/2020 | Salazar et al. |
| 10,765,343 | B2 | 9/2020 | Henkel et al. |
| 2020/0305982 | A1 * | 10/2020 | Akbarian ........... A61B 17/1633 |
| 2022/0061927 | A1 | 3/2022 | Sramek et al. |

* cited by examiner

*Primary Examiner* — Scott Luan
(74) *Attorney, Agent, or Firm* — Morgan, Lewis & Bockius LLP

(57) ABSTRACT

An apparatus includes a body and the first position sensor. The body defines a bore sized to receive a portion of a medical instrument having a rotary member. The rotary member is configured to generate interference in an electromagnetic field while rotating about a longitudinal axis. The body is configured to be fixedly secured to the medical instrument while allowing rotation of the rotary member about the longitudinal axis. The first position sensor is supported by the body and is configured to generate a signal indicating a position of the first position sensor in three-dimensional space. The first position sensor is oriented to offset the interference generated by the rotary member.

20 Claims, 25 Drawing Sheets

MEDICAL INSTRUMENT WITH ROTARY END EFFECTOR, POSITION SENSOR, AND ELECTROMAGNETIC INTERFERENCE REDUCTION

PRIORITY

This application claims priority to U.S. Provisional Pat. App. No. 63/464,264, entitled "Medical Instrument with Rotary End Effector, Position Sensor, and Electromagnetic Interference Reduction," filed May 5, 2023, the disclosure of which is incorporated by reference herein, in its entirety.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation system that may be used in IGS procedures is the CARTO® 3 System by Biosense-Webster, Inc., of Irvine, California. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, some instruments can include sensors (e.g., electromagnetic coils that emit electromagnetic fields and/or are responsive to externally generated electromagnetic fields), which can be used to perform the procedure while the sensors send data to the computer indicating the current position of each sensor-equipped instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

In some scenarios, it may be desirable to remove tissue and bone from within a nasal cavity of a patient. Some such procedures may be known as functional endoscopic sinus surgery (FESS). Such procedures may be performed using various instruments, such as microburs, shavers, drills, microdebriders, etc. In some such procedures, an endoscope may provide at least some degree of visualization of the surgical field. However, given the confines of the nasal cavity, it may be desirable to provide additional navigation guidance to the instrument via an IGS navigation system. Rotary instruments such as those listed above may also be used in an otological context, such as during nerotology/ lateral skull-based procedures. In such procedures, the options for providing endoscopic visualization may be even more limited than in the nasal cavity. While several systems and methods have been made and used in connection with IGS navigation systems, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Example of an Image Guided Surgery Navigation System

Figure 1:
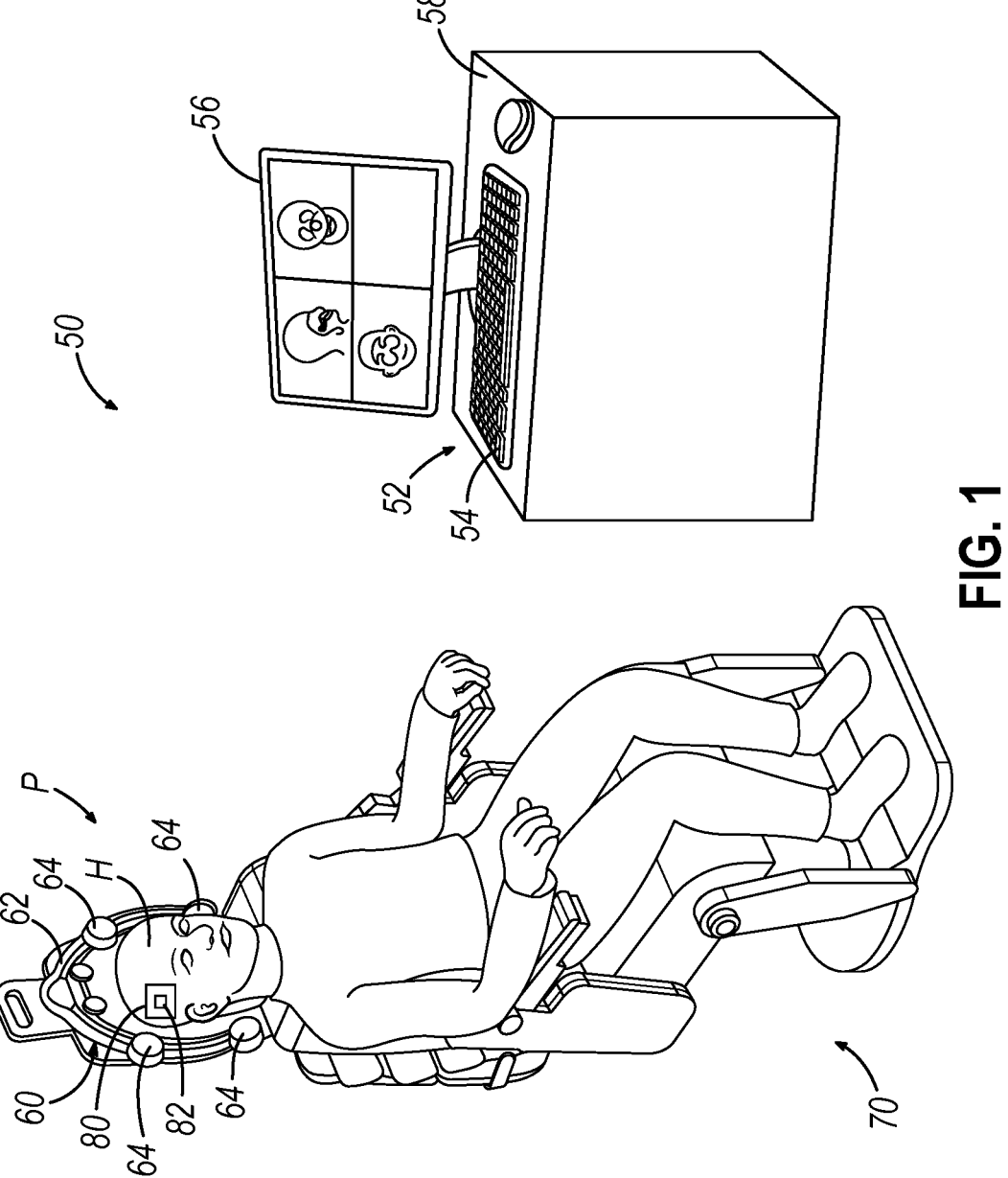
FIG. 1 depicts a schematic view of an example of a surgery navigation system being used on a patient seated in an example of a medical procedure chair.

When performing a medical procedure within a head of a patient (P), it may be desirable to have information regarding the position of an instrument within the head (H) of the patient (P), particularly when the instrument is in a location where it is difficult or impossible to obtain an endoscopic view of a working element of the instrument within the head of the patient (P). FIG. 1 shows an example of an IGS navigation system (50) enabling a medical procedure to be performed within a head (H) of a patient (P) using image guidance. In addition to or in lieu of having the components and operability described herein IGS navigation system (50) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein, in its entirety; and/or U.S. Pat. No. 10,561,370, entitled "Apparatus to Secure Field Generating Device to Chair," issued Feb. 18, 2020, the disclosure of which is incorporated by reference herein, in its entirety.

IGS navigation system (50) of the present example comprises a field generator assembly (60), which comprises a set of magnetic field generators (64) that are integrated into a horseshoe-shaped frame (62). Field generators (64) are operable to generate alternating magnetic fields of different frequencies around the head (H) of the patient (P). An instrument may be inserted into the head (H) of the patient (P). Such an instrument may include one or more position sensors as described in greater detail below. In the present example, frame (62) is mounted to a chair (70), with the patient (P) being seated in the chair (70) such that frame (62) is located adjacent to the head (H) of the patient (P). By way of example only, chair (70) and/or field generator assembly (60) may be configured and operable in accordance with at least some of the teachings of U.S. Pat. No. 10,561,370, entitled "Apparatus to Secure Field Generating Device to Chair," Issued Feb. 18, 2020, the disclosure of which is incorporated by reference herein, in its entirety. In some other variations, the patient (P) lies on a table; and field generator assembly (60) is positioned on or near the table.

IGS navigation system (50) of the present example further comprises a processor (52), which controls field generators (64) and other elements of IGS navigation system (50). For instance, processor (52) is operable to drive field generators (64) to generate alternating electromagnetic fields; and process signals from the instrument to determine the location of a navigation sensor or position sensor in the instrument within the head (H) of the patient (P). Processor (52) comprises a processing unit (e.g., a set of electronic circuits arranged to evaluate and execute software instructions using combinational logic circuitry or other similar circuitry) communicating with one or more memories. Processor (52) of the present example is mounted in a console (58), which comprises operating controls (54) that include a keypad and/or a pointing device such as a mouse or trackball. A physician uses operating controls (54) to interact with processor (52) while performing the surgical procedure.

While not shown, the instrument that is used with IGS navigation system (50) may include a navigation sensor or position sensor that is responsive to positioning within the alternating magnetic fields generated by field generators (64). A coupling unit (not shown) may be secured to the proximal end of the instrument and may be configured to provide communication of data and other signals between console (58) and the instrument. The coupling unit may provide wired or wireless communication of data and other signals.

In some versions, the navigation sensor or position sensor of the instrument may comprise at least one coil at or near the distal end of the instrument. When such a coil is positioned within an alternating electromagnetic field generated by field generators (64), the alternating magnetic field may generate electrical current in the coil, and this electrical current may be communicated along the electrical conduit(s) in the instrument and further to processor (52) via the coupling unit. This phenomenon may enable IGS navigation system (50) to determine the location of the distal end of the instrument within a three-dimensional space (i.e., within the head (H) of the patient (P), etc.). To accomplish this, processor (52) executes an algorithm to calculate location coordinates of the distal end of the instrument from the position related signals of the coil(s) in the instrument. Thus, a navigation sensor may serve as a position sensor by generating signals indicating the real-time position of the sensor within three-dimensional space.

Processor (52) uses software stored in a memory of processor (52) to calibrate and operate IGS navigation system (50). Such operation includes driving field generators (64), processing data from the instrument, processing data from operating controls (54), and driving display screen (56). In some implementations, operation may also include monitoring and enforcement of one or more safety features or functions of IGS navigation system (50). Processor (52)

is further operable to provide video in real time via display screen (56), showing the position of the distal end of the instrument in relation to a video camera image of the patient's head (H), a CT scan image of the patient's head (H), and/or a computer-generated three-dimensional model of the anatomy within and adjacent to the patient's nasal cavity. Display screen (56) may display such images simultaneously and/or superimposed on each other during the surgical procedure. Such displayed images may also include graphical representations of instruments that are inserted in the patient's head (H), such that the operator may view the virtual rendering of the instrument at its actual location in real time. By way of example only, display screen (56) may provide images in accordance with at least some of the teachings of U.S. Pat. No. 10,463,242, entitled "Guidewire Navigation for Sinuplasty," issued Nov. 5, 2019, the disclosure of which is incorporated by reference herein, in its entirety. In the event that the operator is also using an endoscope, the endoscopic image may also be provided on display screen (56). The images provided through display screen (56) may help guide the operator in maneuvering and otherwise manipulating instruments within the patient's head (H).

In the present example, field generators (64) are in fixed positions relative to the head (H) of the patient (P), such that the frame of reference for IGS navigation system (50) (i.e., the electromagnetic field generated by field generators (64)) does not move with the head (H) of the patient (P). In some instances, the head (H) of the patient (P) may not remain completely stationary relative to field generators (64) throughout the duration of a medical procedure, such that it may be desirable to track movement of the head (H) of the patient (P) during a medical procedure. To that end, a patient tracking assembly (80) is secured to the head (H) of the patient (P) in this example. Patient tracking assembly (80) may be secured to the head (H) via an adhesive, via one or more screws, or in any other suitable fashion. Patient tracking assembly (80) includes a position sensor (82), which is in communication with processor (52), such as via a cable (84) (see FIGS. 4-7). In some versions, position sensor (82) is wirelessly coupled with processor (52), such that cable (84) is omitted.

Position sensor (82) is configured to generate signals indicating the real-time position of position sensor (82) in response to an alternating electromagnetic field generated by field generators (64). By way of example only, position sensor (82) may comprise one or more coils. The signals generated by position sensor (82) are communicated to processor (52), such that processor (52) may process signals from position sensor (82) to determine the real-time position of position sensor (82) in three-dimensional space. With patient tracking assembly (80) being firmly secured to the head (H) of the patient (P), patient tracking assembly (80) may move unitarily with the head (H) of the patient (P). Accordingly, signals from position sensor (82) may effectively indicate the real-time position of the head (H) of the patient in three-dimensional space.

After patient tracking assembly (80) is secured to the head (H) of the patient (P), an operator may insert one or more position sensor equipped medical instruments (e.g., ENT shaver, suction cannula, balloon dilation catheter, electrosurgical instrument, etc.) into the head (H) of the patient (P). Signals from position sensors of such instruments may be communicated to processor (52), thereby enabling processor (52) to determine the real-time positions of such instruments in three-dimensional space. With processor (52) knowing the real-time position of the head (H) of the patient (P) in three-dimensional space based on signals from position sensor (82), and with processor (52) knowing the real-time position of a medical instrument in three-dimensional space based on signals from one or more position sensors in the medical instrument, processor (52) may accurately determine the real-time position of the medical instrument in the head (H) of the patient (P). Processor (52) may thereby drive display screen (56) to display an indicator (e.g., crosshairs, etc.) showing the real-time position of the medical instrument in the head (H) of the patient (P) as described above. By way of example only, processor (52) may drive display screen (56) to display an indicator (e.g., crosshairs, etc.) to show the real-time position of the medical instrument in the head (H) of the patient (P) as an overlay on one or more images of at least a portion of the head (H) of the patient (P).

II. Example of Rotary ENT Instrument

Figure 2:
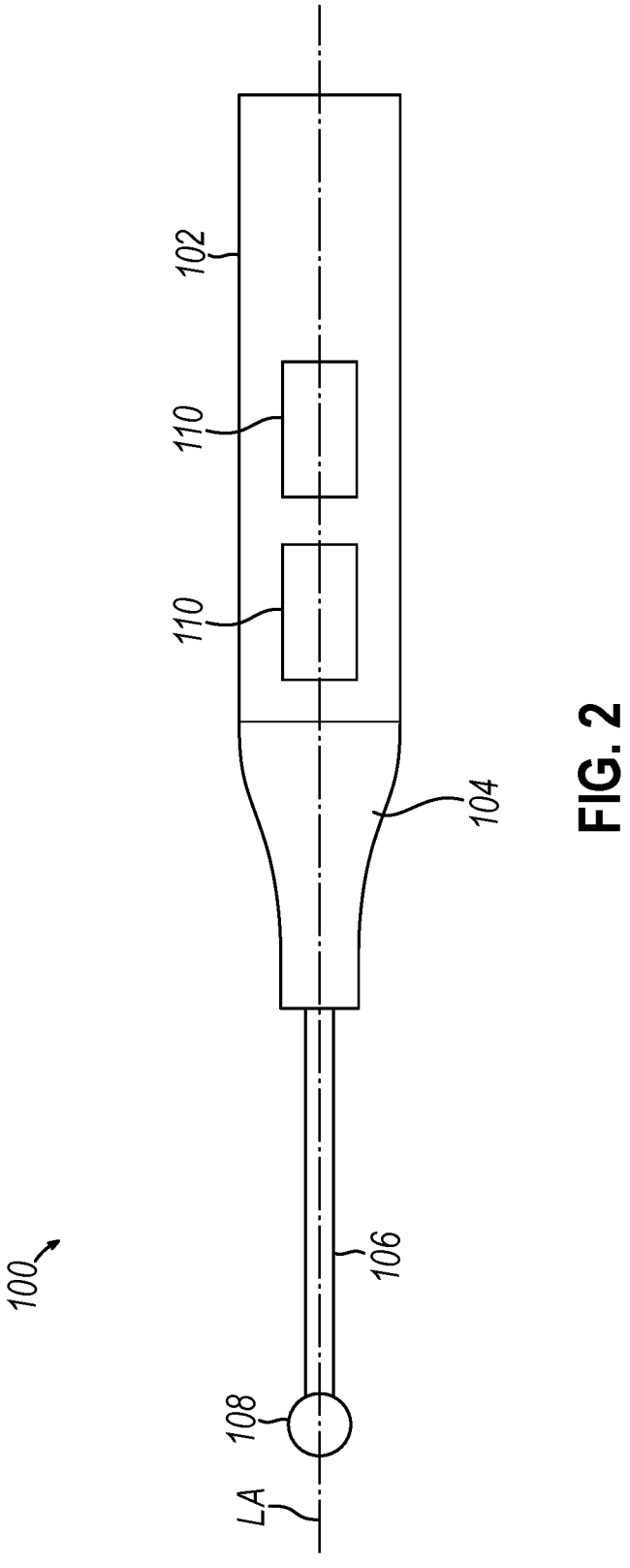
FIG. 2 depicts a schematic side view of an example of a rotary ear nose and throat (ENT) instrument.

As noted above, some ENT procedures include use of a medical instrument with a rotary feature, such as a microbur, shaver, drill, microdebrider, etc. Such instruments may be used to remove tissue, and in some cases bone, from within a nasal cavity in a FESS procedure or other procedure, in a nerotology/lateral skull-based procedure, or elsewhere in an ear, nose, or throat. An example of a rotary ENT instrument (100) is shown in FIG. 2. Instrument (100) of this example includes a body (102), a nose portion (104), a shaft assembly (106), and an end effector (108). Body (102) is configured for grasping by a hand of a human operator, though other versions of body (102) may be configured to engage a robotic arm. Nose portion (104) is positioned at a distal end of body (102) and provides a contoured or tapered transition toward shaft assembly (106). Shaft assembly (106) may consist of a single shaft, or may comprise two or more shafts and/or other components. For instance, some variations of shaft assembly (106) may include an inner shaft that is rotatable relative to body (102) and an outer shaft that is non-rotatable relative to body (102) and thus forms a sheath around the rotary inner shaft.

End effector (108) is disposed at the distal end of shaft assembly (106). End effector (108) may take various forms. In some versions, end effector (108) comprises a bur. In some other versions, end effector (108) comprises a shaver or debrider head. In still other versions, end effector (108) comprises a drill bit. Alternatively, end effector (108) may take any other suitable form. End effector (108) of the present example is configured to rotate about a longitudinal axis (LA) of instrument (100). In particular, at least a portion of shaft assembly (106) is operable to drive rotation of end effector (108). By way of example only, end effector (108) may be rotated about longitudinal axis (LA) at an angular velocity of up to about 80,000 rpm; or in some cases faster than about 80,000 rpm. In the present example, this rotation is driven by a motor (110) that is disposed in body (102). In some other versions, motor (110) is external to body (102). In some such versions, a rotary drive cable and/or other form of drivetrain couples motor (110) with a rotary drive feature of shaft assembly (106), to thereby drive rotation of end effector (108). Instrument (100) of the present example further includes an internal power source (112) (e.g., battery or set of batteries, etc.) that is operable to power motor (110). Power source (112) is positioned in body (102). In some other variations, power source (112) is external to body (102).

III. Example of Navigation Adapter for Rotary ENT Instrument

As noted above, it may be beneficial to utilize IGS navigation system (50) to assist an operator in navigating a medical instrument within the head (H) of a patient (P). In some scenarios where a rotary ENT instrument like instrument (100) is used, instrument (100) may lack any integral position sensors, such that instrument (100) lacks compatibility with IGS navigation system (50). Modifying a rotary ENT instrument like instrument (100) to include one or more position sensors that are compatible with IGS navigation system (50) may present difficulties, however. For instance, in some cases, shaft assembly (106) and end effector (108) are metallic, such that shaft assembly (106) and end effector (108) may tend to generate electromagnetic interference within the electromagnetic fields generated by field generator assembly (60). Such interference may be particularly enhanced when at least a portion of shaft assembly (106) and end effector (108) are rotated at high angular velocities (e.g., approximately 80,000 rpm or higher). It may therefore be desirable to integrate position sensors into instrument (100) in such a way to minimize or avoid electromagnetic interference from shaft assembly (106) and end effector (108) when instrument (100) is activated.

It may also be desirable to enable integration of one or more position sensors into instrument (100) in a retrofit fashion. In other words, rather than manufacturing a variation of instrument (100) with one or more position sensors fully integrated therein, it may be desirable to provide a navigation adapter that may be selectively fitted to instrument (100) as desired by the operator. This may be particularly desirable for versions of instrument (100) that are reusable but might not otherwise be reusable if such versions of instrument had one or more fully integrated position sensors. This may also be particularly desirable to minimize the cost of instrument (100), such that a navigation adapter may only be purchased added to instrument (100) if and when compatibility with IGS navigation system (50) is desired.

Figure 3:
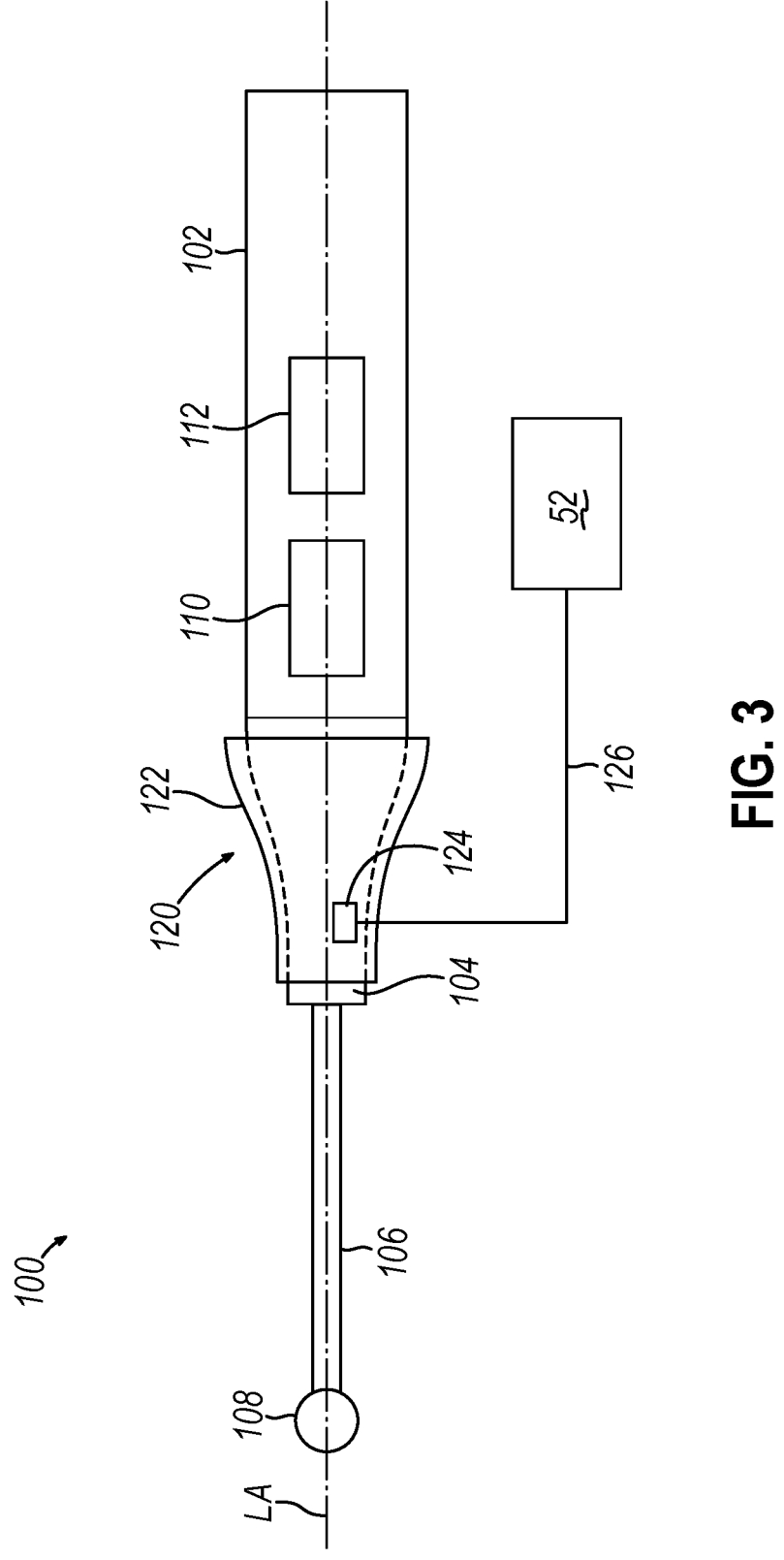
FIG. 3 depicts a schematic side view of an example of a navigation adapter secured to the rotary ENT instrument of FIG. 2.
Figure 4:
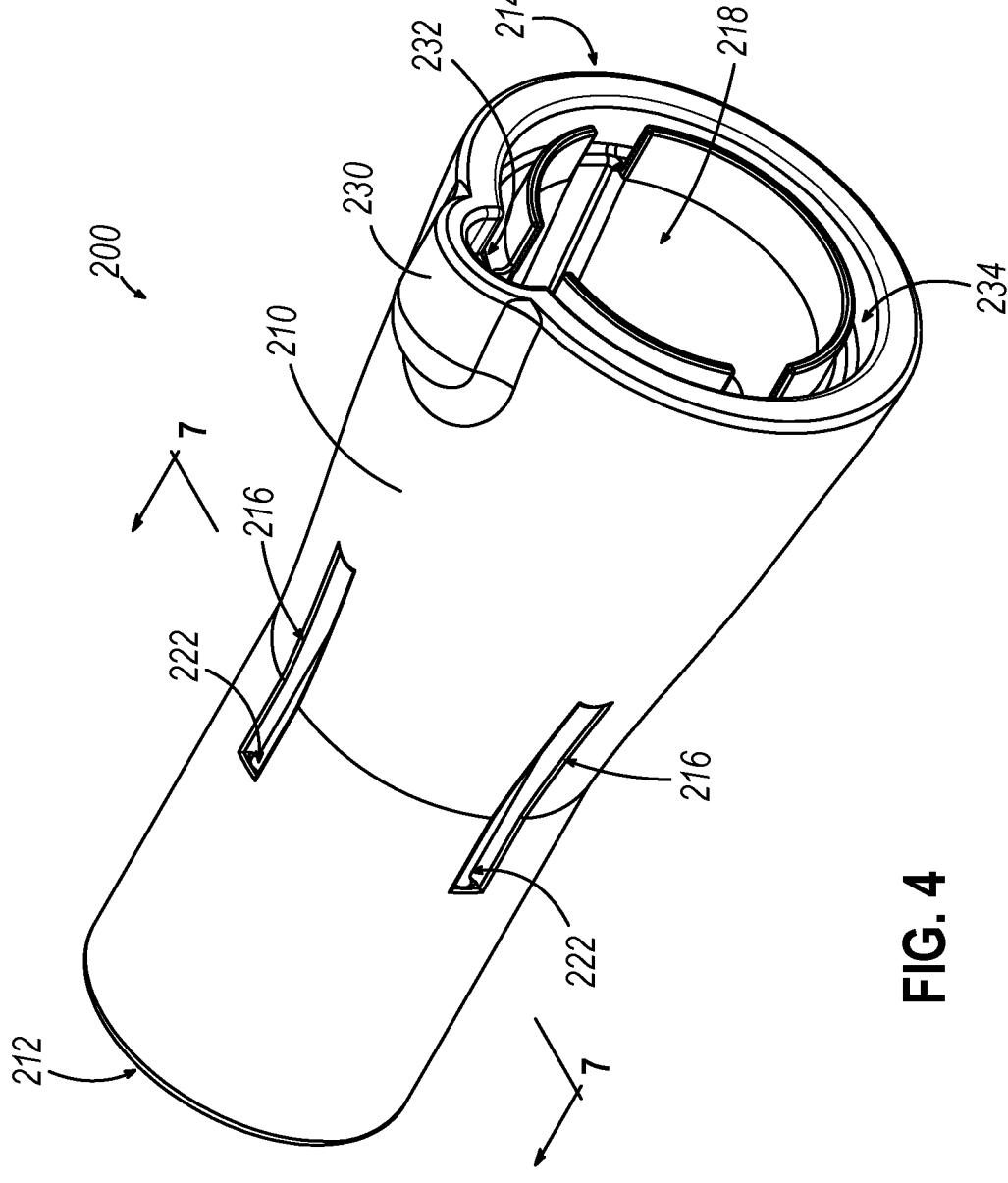
FIG. 4 depicts a perspective view of another example of a navigation adapter that may be secured to the rotary ENT instrument of FIG. 2.

FIG. 3 shows a schematic representation of a navigation adapter (120) that may be selectively coupled with instrument (100) to provide compatibility with IGS navigation system (50). Navigation adapter (120) of this example includes a body (122) with an integral position sensor (124). Body (122) is configured to be secured to nose portion (104). By way of example only, body (122) may be secured to nose portion (104) via one or more adhesives, via a friction fit (which may be enhanced through one or more elastomeric features), via a snap fit, or in any other suitable fashion. In some versions, body (122) is configured to be removable from nose portion (104) after being secured to nose portion (104), without destroying body (122) or nose portion (104). In some other versions, body (122) is configured to be permanently secured to portion (104) after being secured to nose portion (104), such that body (122) cannot be subsequently removed from nose portion (104) without destroying body (122) or nose portion (104). Various suitable ways in which body (122) may be secured to nose portion (104) will be apparent to those skilled in the art in view of the teachings herein.

Position sensor (124) of the present example includes one or more coils. When such a coil is positioned within an alternating electromagnetic field generated by field generators (64), the alternating magnetic field may generate electrical current in the coil, and this electrical current may be communicated along a cable (126) to processor (52). This phenomenon may enable IGS navigation system (50) to determine the real-time position of position sensor (124) within a three-dimensional space (i.e., within the head (H) of the patient (P), etc.). While signals are communicated from position sensor (124) to processor (52) via cable (126) in this example, some other versions may provide wireless communication of signals from position sensor (124) to processor (52).

In some versions, position sensor (124) comprises three single-axis coils. In some other versions, position sensor (124) comprises two single-axis coils. In some other versions, position sensor (124) comprises a dual-axis coil arrangement. In some other versions, position sensor (124) comprises a concentric three-axis coil arrangement. In some other versions, position sensor (124) comprises a non-concentric three-axis coil arrangement.

In the present example, position sensor (124) is rigidly secured relative to nose portion (104); and shaft assembly (106) and end effector (108) are both rigid. Thus, the distance between position sensor (124) and end effector (108) may be fixed during operation of instrument (100). To the extent that this fixed distance is "known" by processor (52), processor (52) may readily determine the real-time position of end effector (108) within a three-dimensional space (i.e., within the head (H) of the patient (P), etc.) based on the position-indicative signals from position sensor (124). In other words, processor (52) may extrapolate the real-time position of end effector (108) based on the real-time position of position sensor (124). In cases where multiple position sensors (124) are used, or where position sensor (124) comprises a plurality of coils wrapped about different respective axes, processor (52) may further determine the orientation of end effector (108) and shaft assembly (106).

As noted above, shaft assembly (106) and end effector (108) may tend to generate electromagnetic interference within the electromagnetic fields generated by field generator assembly (60), particularly when at least a portion of shaft assembly (106) and end effector (108) are rotated at high angular velocities (e.g., approximately 80,000 rpm or higher), and particularly when at least a portion of shaft assembly (106) and end effector (108) comprise ferromagnetic material (e.g., steel). Navigation adapter (120) may minimize or eliminate effects of such interference with respect to position sensor (104) by orienting position sensor (104) at a certain orientation relative to the central longitudinal axis (LA). In particular, position sensor (104) may be oriented such that the effective area of position sensor (104) is orthogonal to the electromagnetic field interference generated by shaft assembly (106) and end effector (108). Such an orthogonal orientation may reduce or prevent the electromagnetic flux of the interference generated by shaft assembly (106) and end effector (108). In addition, the length of position sensor (104) may be selected to maximize the isolation of position sensor (104) from the electromagnetic flux of the interference generated by shaft assembly (106) and end effector (108).

The following description provides specific examples of how variations of navigation adapter (120) may be configured. It should be understood that the following examples are just illustrative, such that navigation adapter (120) may alternatively be configured in numerous other ways.

A. Example of First Variation of Navigation Adapter

FIGS. 4-8 show an example of a form that navigation adapter (120) may take. In particular, FIGS. 4-8 show a navigation adapter (200) that comprises a body (210) having a distal end (212), a proximal end (214), and a bore (218) formed therethrough. Body (210) may be selectively secured to nose portion (104) like body (122) of navigation adapter described above, such that bore (218) is sized to receive nose portion (104). Body (210) may include one or more internal elastomeric features that are configured to provide a snug fit with nose portion (104) when navigation adapter (200) is fully seated on nose portion (104), such that body (210) may be secured to nose portion (104) through friction. Alternatively, body (210) may be secured to nose portion (104) in any other suitable fashion.

Figure 5:
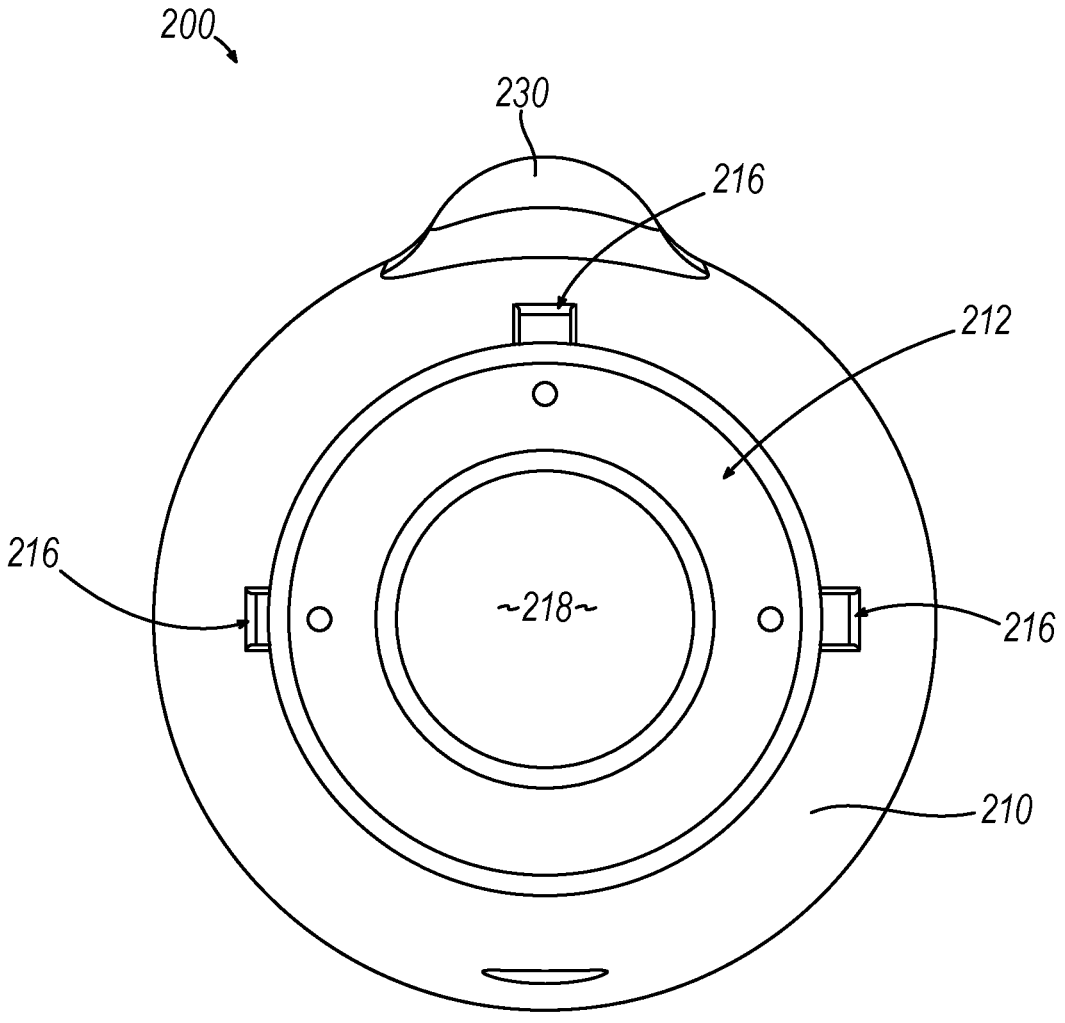
FIG. 5 depicts a front end view of the navigation adapter of FIG. 4.
Figure 6:
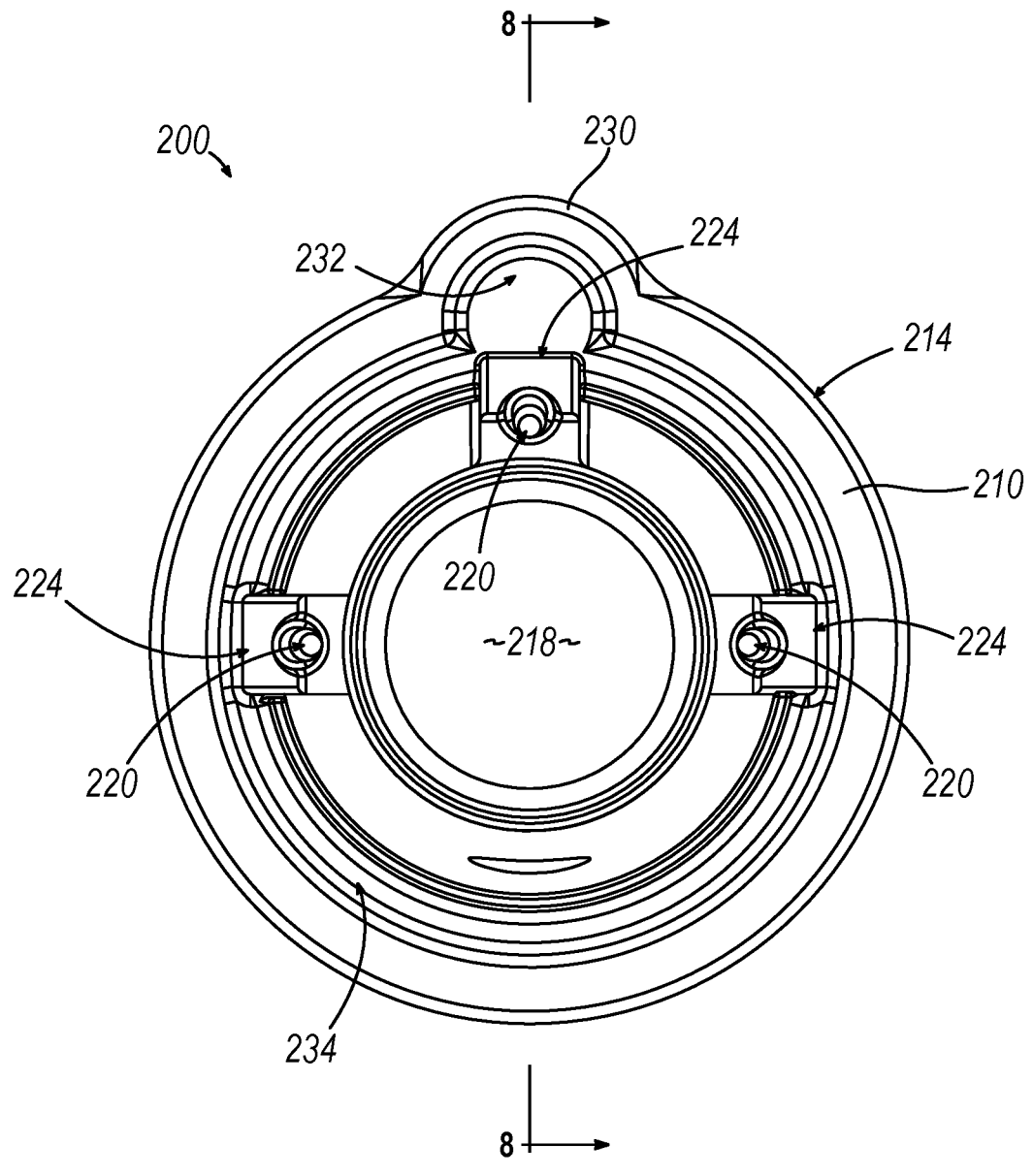
FIG. 6 depicts a rear end view of the navigation adapter of FIG. 4.
Figure 7:
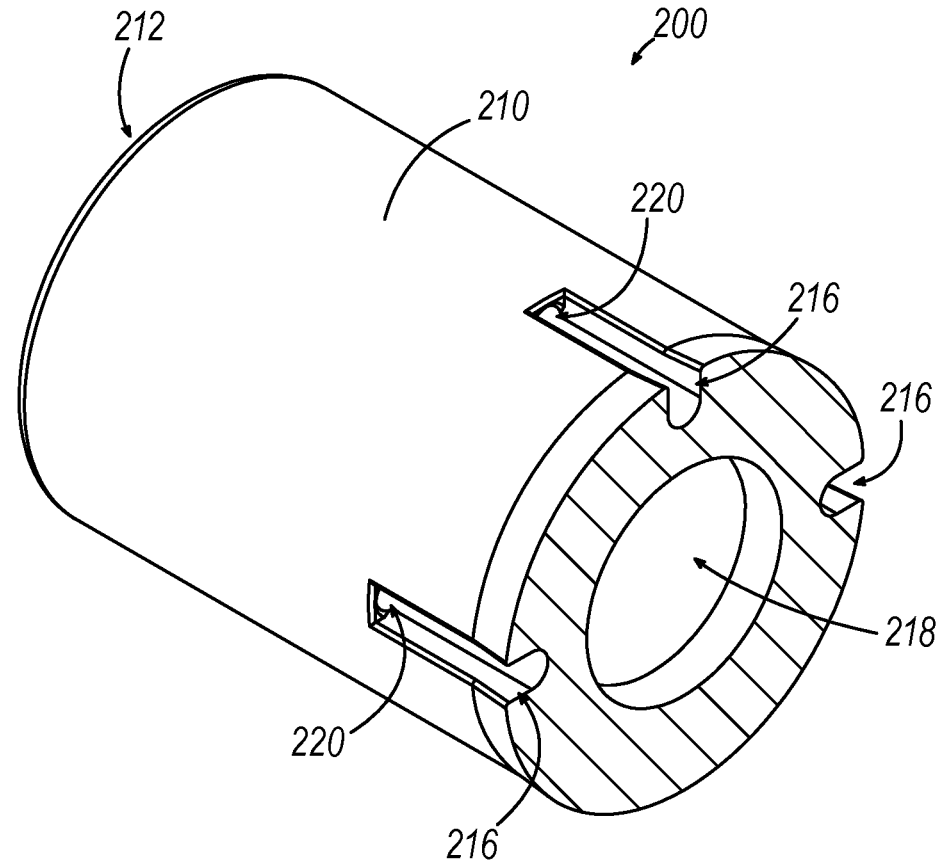
FIG. 7 depicts a cross-sectional perspective view of the navigation adapter of FIG. 4, taken along line 7-7 of FIG. 4.

Body (210) of this example further includes three transversely presented openings (216), with each opening (216) leading to a respective sensor recess (220). In the present example, and as best seen in FIGS. 5-6, opening (216) and recess (220) sets are angularly positioned at 9 o'clock, 12 o'clock, and 3 o'clock about a central longitudinal axis of bore (218), though opening (216) and recess (220) sets may alternatively be spaced in any other suitable arrangement. A protrusion (230) projects laterally from proximal end (214) of body (210) and defines a primary wire passageway (232). Body (210) further defines a proximally facing annular recess (234). As best seen in FIG. 6, annular recess (234) is in communication with secondary wire passageways (224), with each secondary wire passageway (224) ultimately leading to a respective sensor recess (220). Each sensor recess (220) is configured to receive a respective position sensor (not shown). In some versions, the position sensor contained in each sensor recess (220) comprises a single-axis sensor, such that navigation adapter (200) contains a total of three single-axis sensors. Alternatively, the position sensor contained in each sensor recess (220) may have any other suitable number of axes. Each position sensor of navigation adapter (200) may be configured and operable like position sensor (124) of navigation adapter (120) described above. Each position sensor of navigation adapter (200) has a respective wire (not shown) that extends along the corresponding secondary wire passageway (224) and further into annular recess (234). These wires then together exit body (210) via primary wire passageway (232). After leaving body (210) via primary wire passageway (232), the wires may be further coupled with processor (52) via one or more cables (e.g., like cable (126)) or wirelessly.

Figure 8:
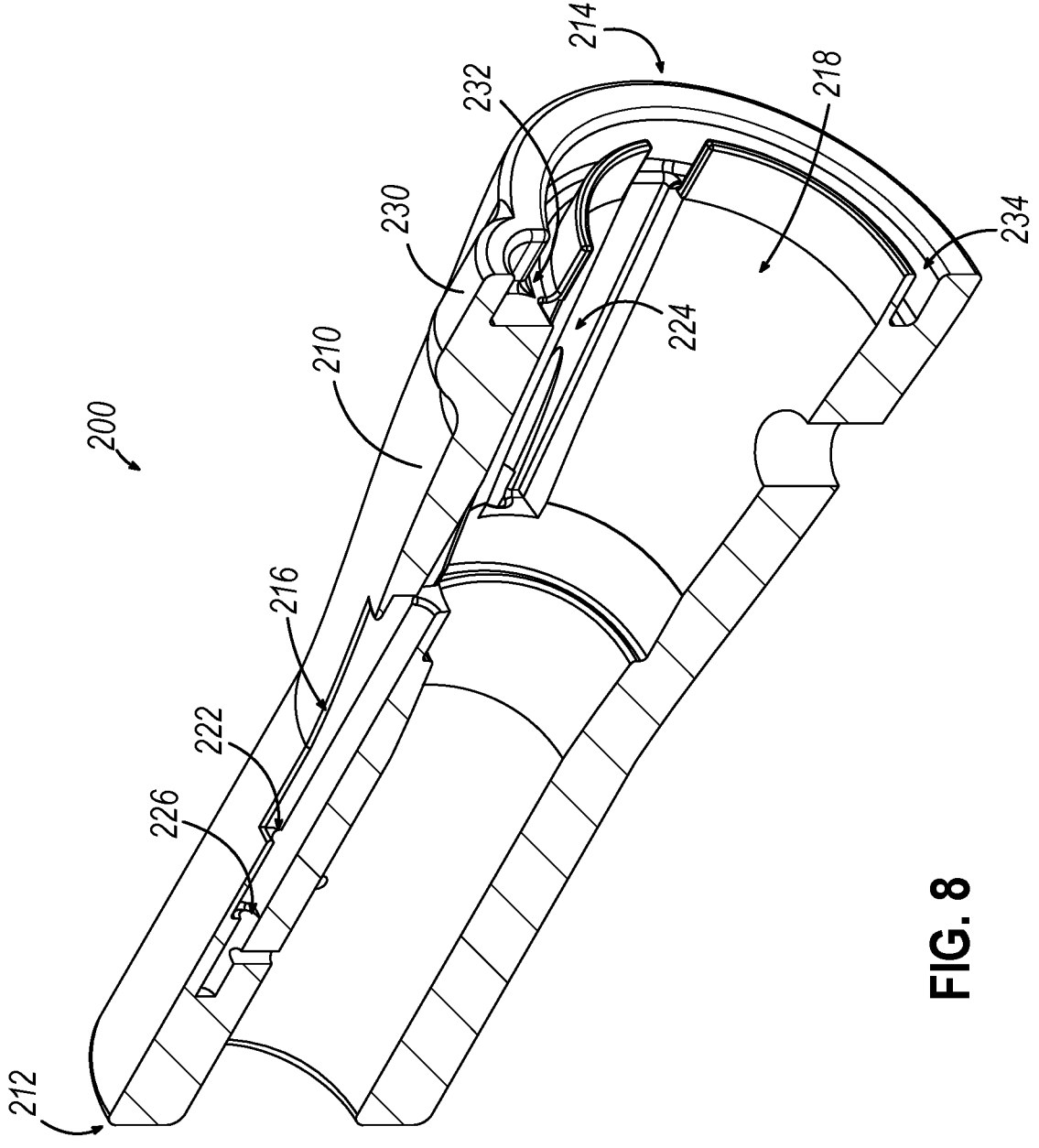
FIG. 8 depicts a cross-sectional perspective view of the navigation adapter of FIG. 4, taken along line 8-8 of FIG. 6.
Figure 9:
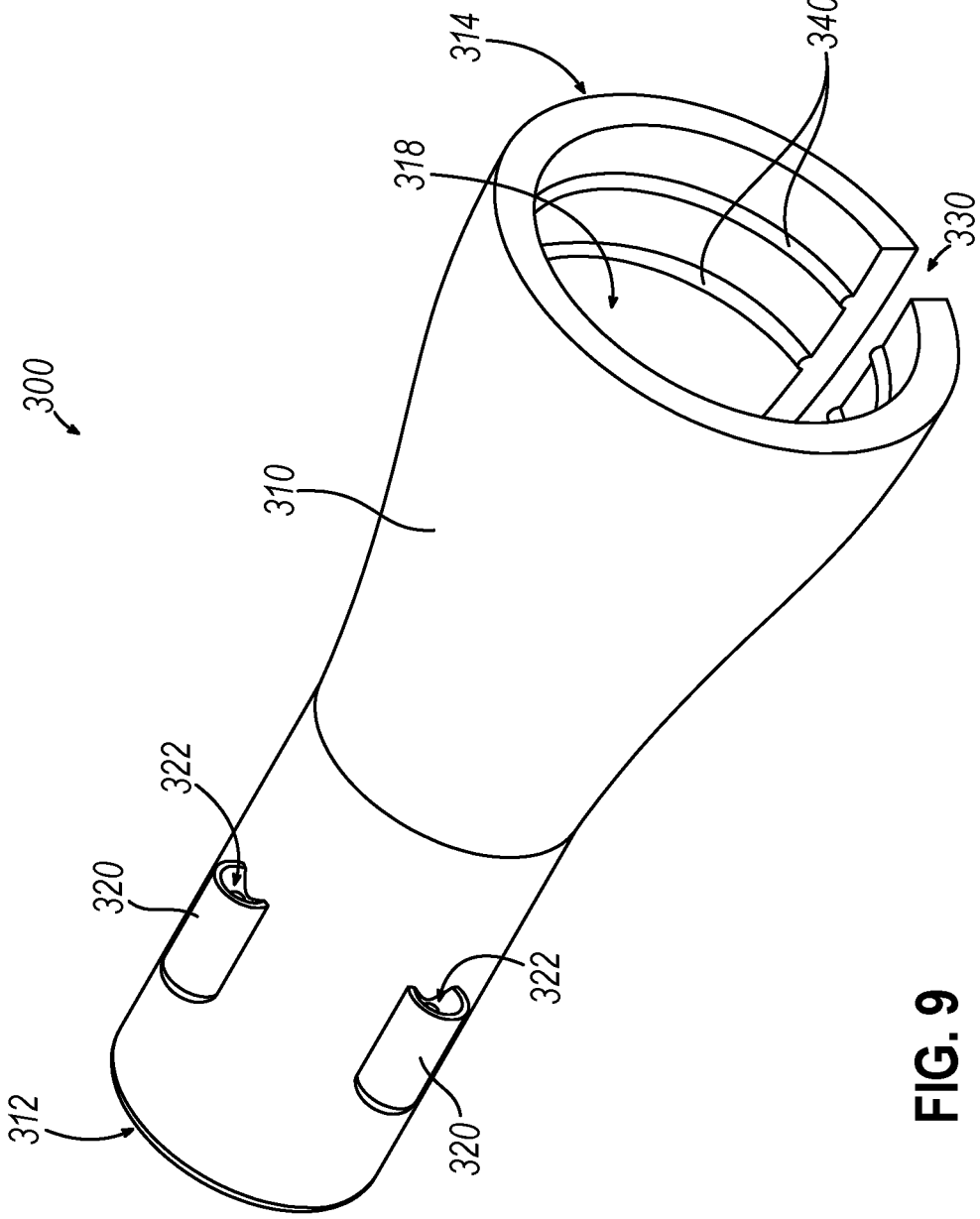
FIG. 9 depicts a perspective view of another example of a navigation adapter that may be secured to the rotary ENT instrument of FIG. 2.
Figure 10:
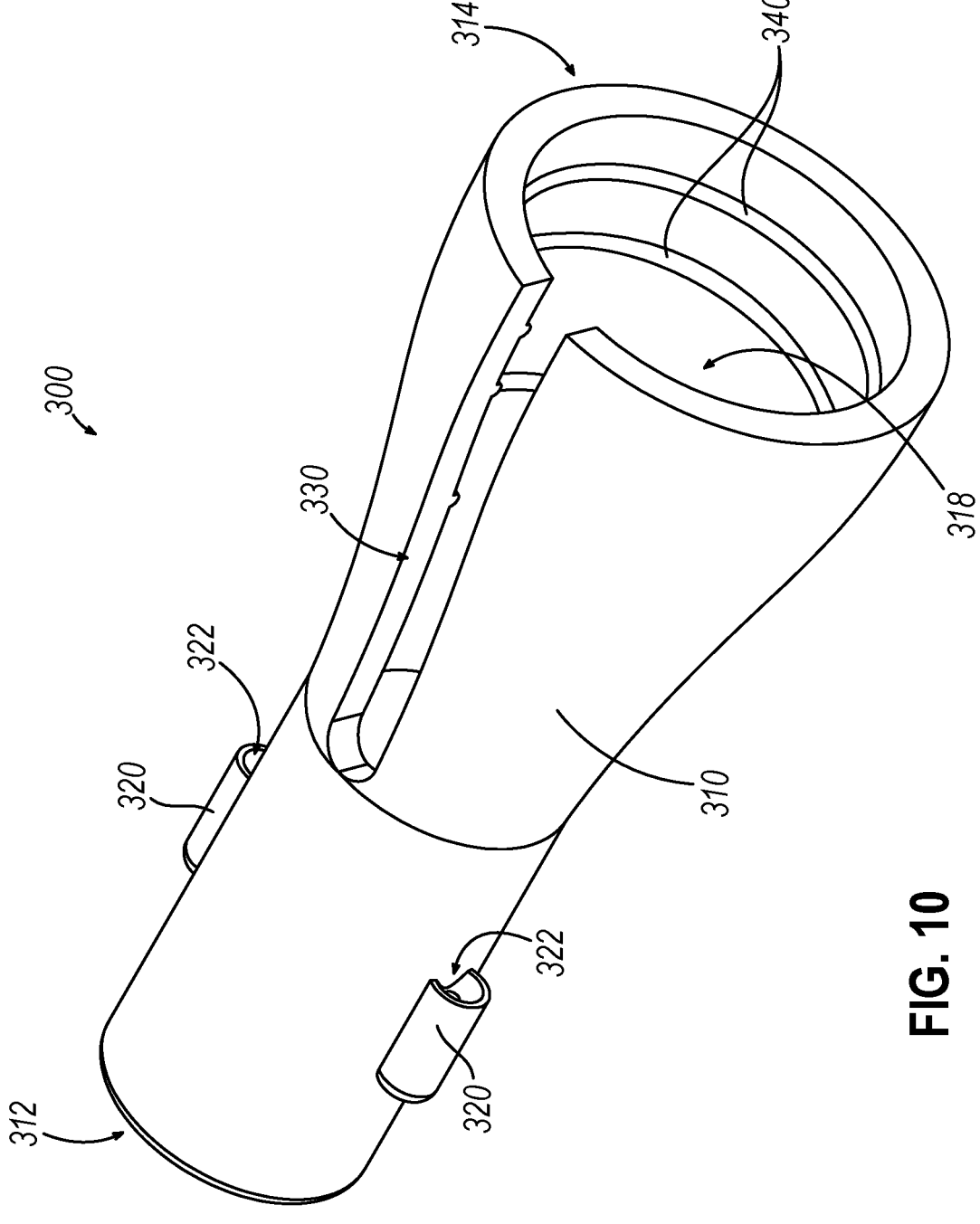
FIG. 10 depicts another perspective view of the navigation adapter of FIG. 9.

As best seen in FIG. 8, each sensor recess (220) further leads to a respective distal recess (226). In some versions, a first portion (e.g., first coil) of each position sensor is positioned in sensor recess (220) while a second portion (e.g., second coil) of the position sensor is positioned in distal recess (226). Alternatively, each recess (220, 226) may be utilized in any other suitable fashion.

B. Example of Second Variation of Navigation Adapter

FIGS. 9-13 show another example of a form that navigation adapter (120) may take. In particular, FIGS. 9-13 show a navigation adapter (300) that comprises a body (310) having a distal end (312), a proximal end (314), and a bore (318) formed therethrough. Body (310) may be selectively secured to nose portion (104) like body (122) of navigation adapter described above, such that bore (318) is sized to receive nose portion (104). Body (310) further includes a set of elastomeric features (340) in the form of longitudinally spaced-apart inner annular protrusions that are configured to provide a snug fit with nose portion (104) when navigation adapter (300) is fully seated on nose portion (104), such that body (310) may be secured to nose portion (104) through friction. By way of example only, elastomeric features (340)

may comprise rubber o-rings. Alternatively, body (310) may be secured to nose portion (104) in any other suitable fashion.

Figure 11:
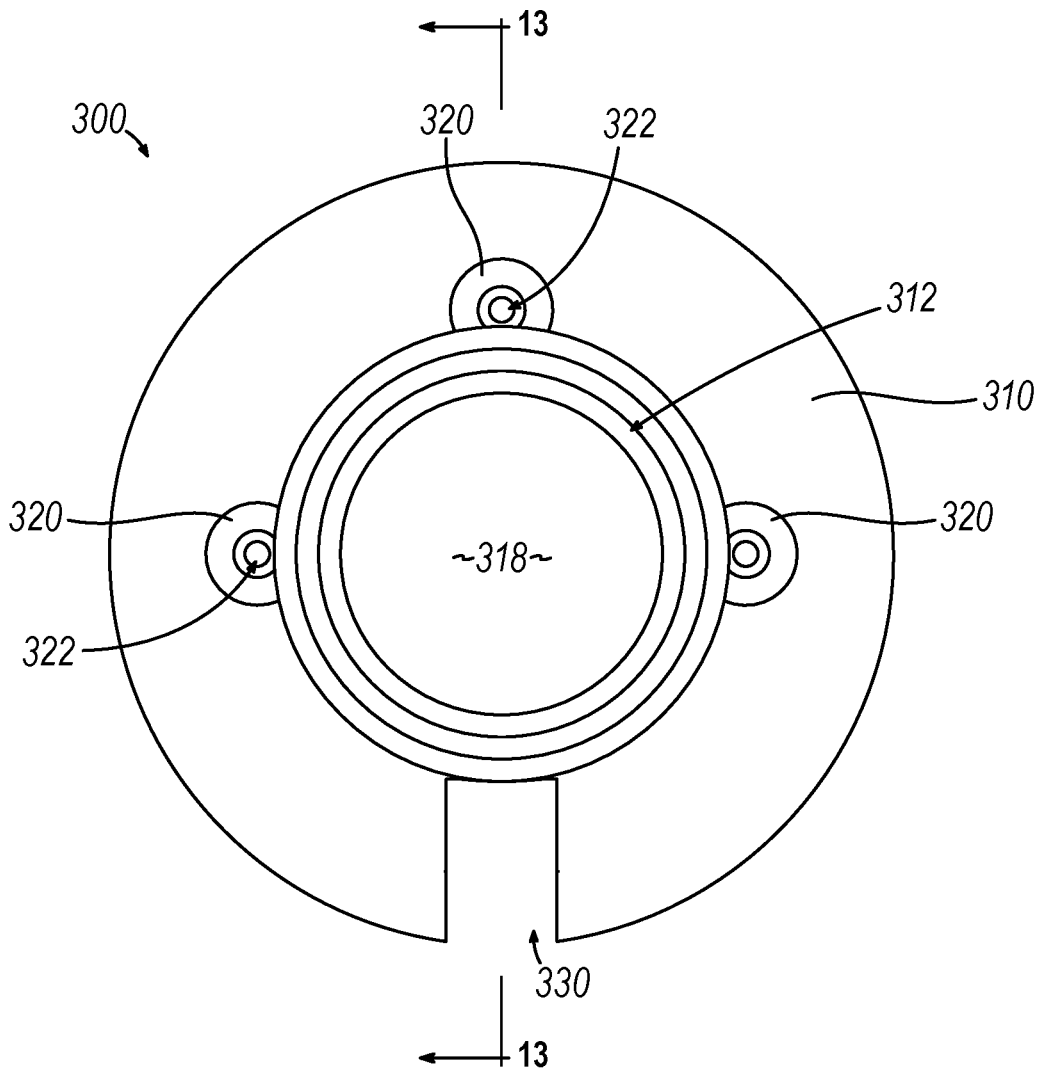
FIG. 11 depicts a front end view of the navigation adapter of FIG. 9.
Figure 12:
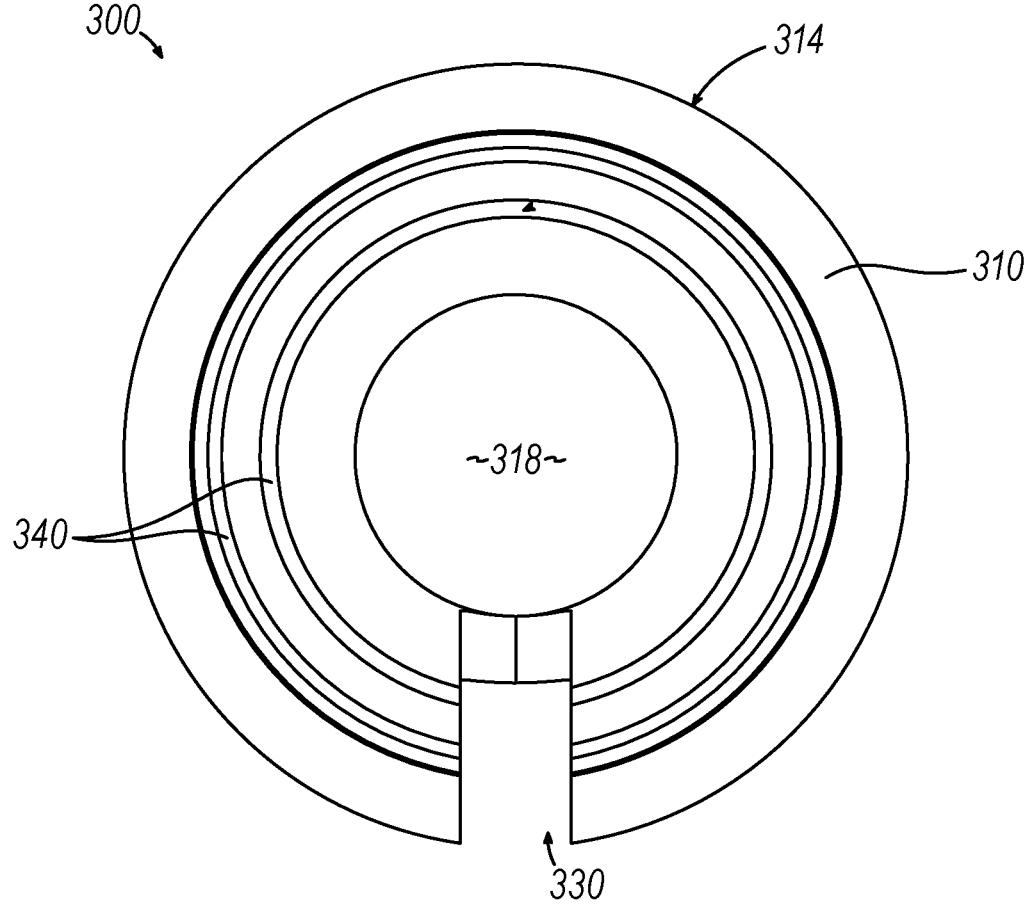
FIG. 12 depicts a rear end view of the navigation adapter of FIG. 9.
Figure 13:
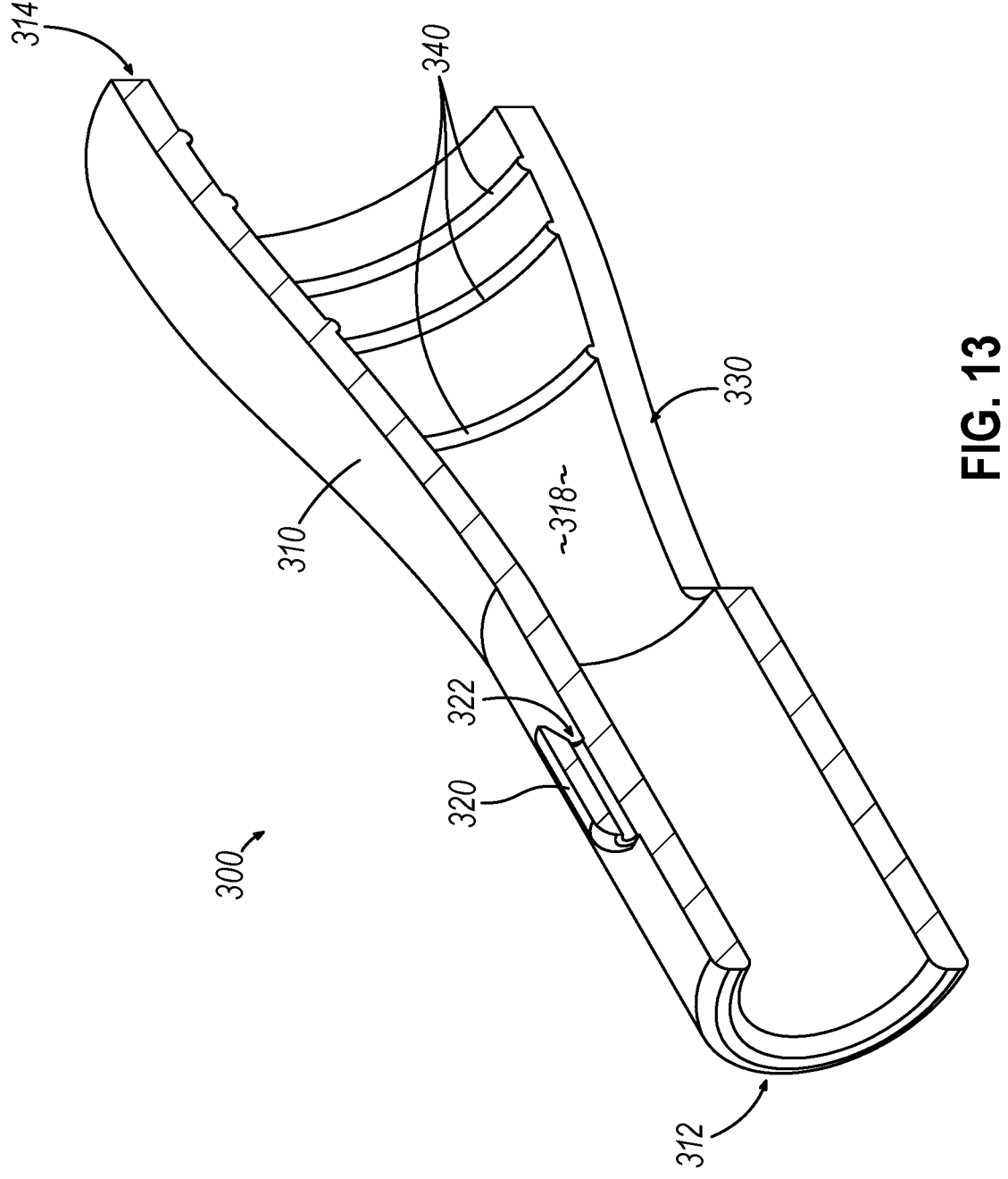
FIG. 13 depicts a cross-sectional perspective view of the navigation adapter of FIG. 4, taken along line 13-13 of FIG. 11.

Body (310) of this example further includes three laterally projecting protrusions (320) near distal end (312), with each protrusion (320) defining a respective sensor recess (322). In the present example, and as best seen in FIG. 11, protrusions (320) and recesses (322) are angularly positioned at 9 o'clock, 12 o'clock, and 3 o'clock about a central longitudinal axis of bore (218), though protrusions (320) and recesses (322) may alternatively be spaced in any other suitable arrangement. Each sensor recess (322) is configured to receive a respective position sensor (not shown). In some versions, the position sensor contained in each sensor recess (322) comprises a single-axis sensor, such that navigation adapter (300) contains a total of three single-axis sensors. Alternatively, the position sensor contained in each sensor recess (322) may have any other suitable number of axes. Each position sensor of navigation adapter (300) may be configured and operable like position sensor (124) of navigation adapter (120) described above. Each position sensor of navigation adapter (300) has a respective wire (not shown) that may be further coupled with processor (52) via one or more cables (e.g., like cable (126)) or wirelessly. In some versions, a heat shrink wrap, tape, cuff, or other member is wrapped about the wires of the position sensors and about body (310) to hold the wires against body (310), though this is merely optional.

A slot (330) extends distally from proximal end (314) of body (310) terminates proximal to distal end (312) of body (310). In some versions, the wires from the position sensors are disposed in slot (330), with a heat shrink wrap, tape, cuff, or other member wrapped about body (310) to keep the wires in slot (330) and against the outer surface of nose portion (104). In addition, or in the alternative, slot (330) may provide clearance for the proximal portion of body (310) to flex outwardly as navigation adapter (300) is pressed onto nose portion (104). In some such versions, a resilience of body (310) urges the outwardly flexed portions of body (310) back inwardly, thereby enhancing the grip of body (310) on nose portion (104).

C. Example of Third Variation of Navigation Adapter

Figure 14:
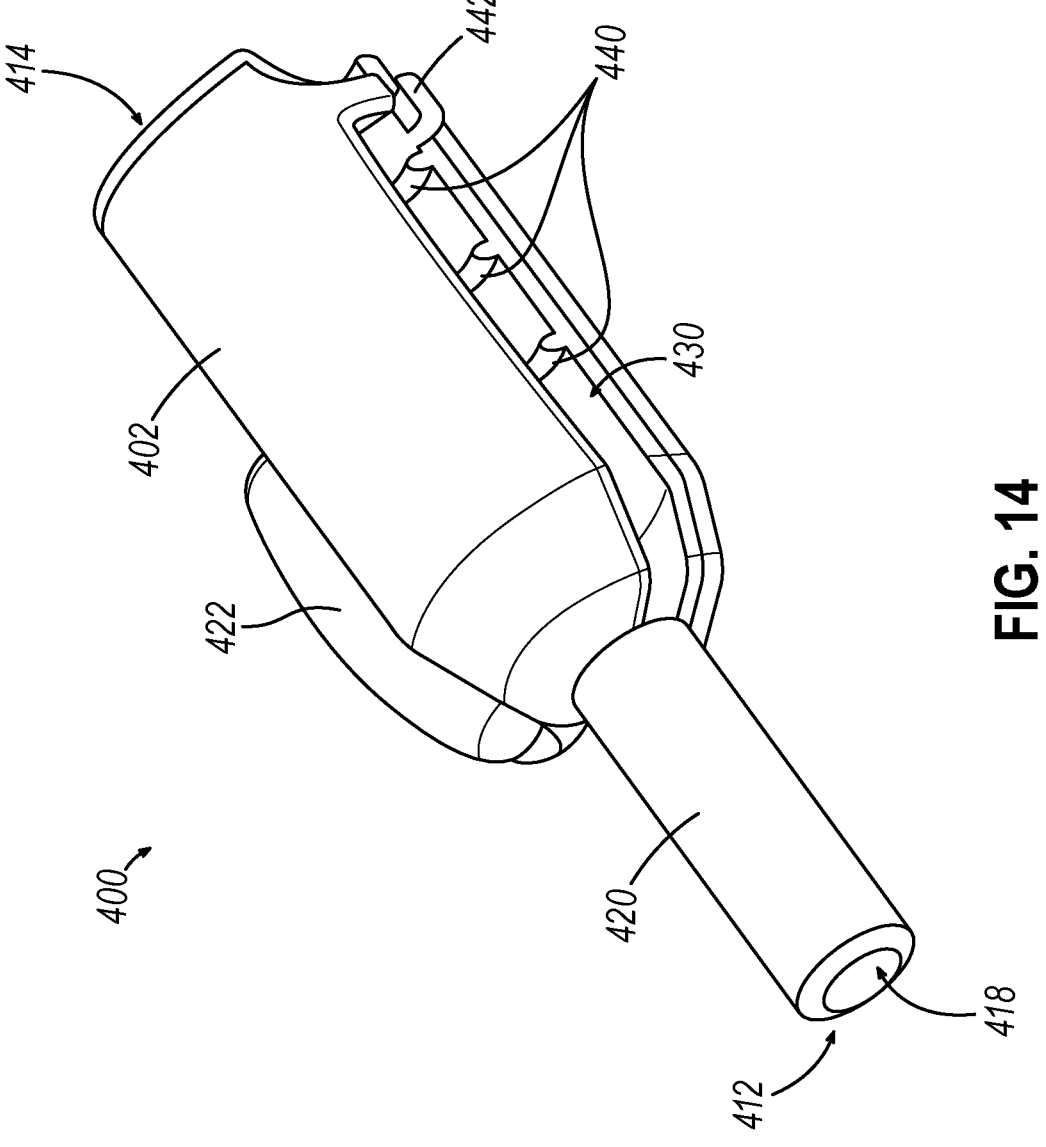
FIG. 14 depicts a perspective view of another example of a navigation adapter that may be secured to the rotary ENT instrument of FIG. 2.
Figure 15:
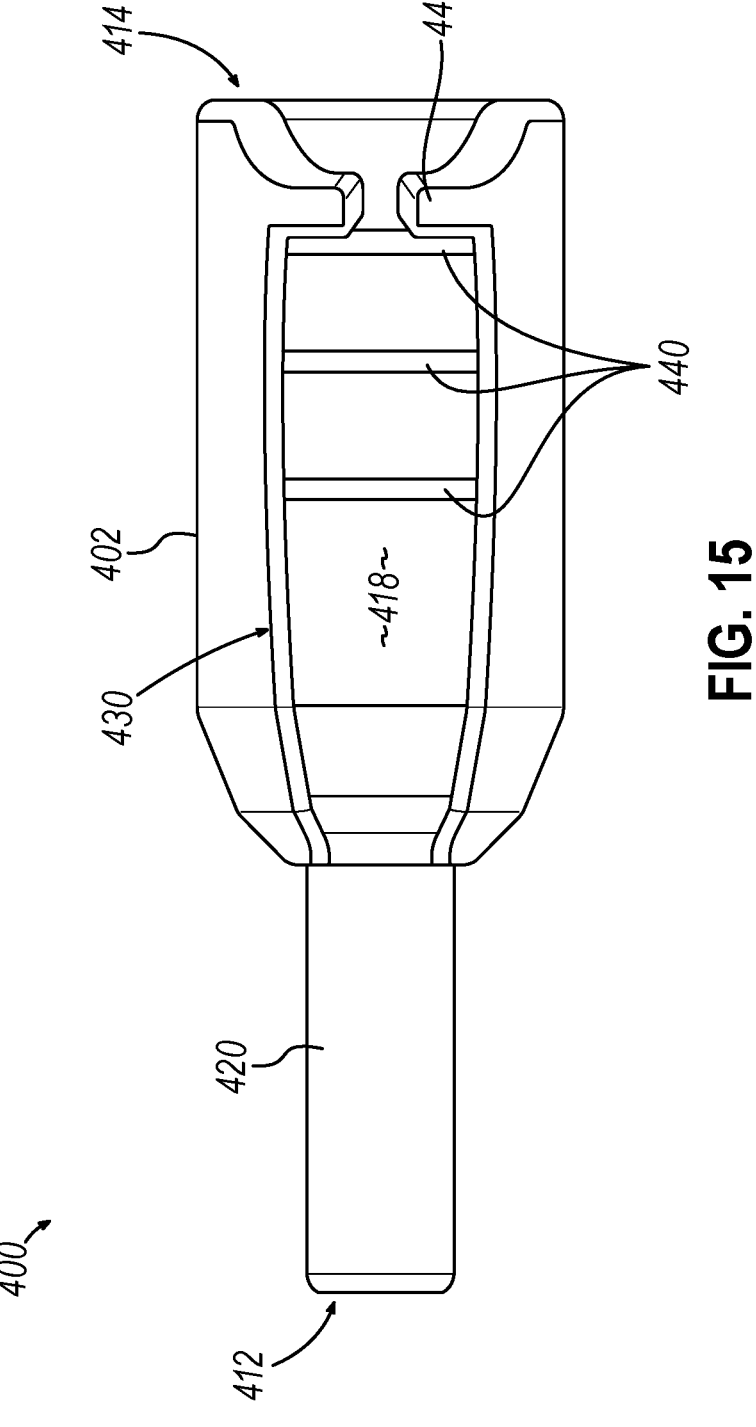
FIG. 15 depicts a bottom plan view of the navigation adapter of FIG. 14.
Figure 16:
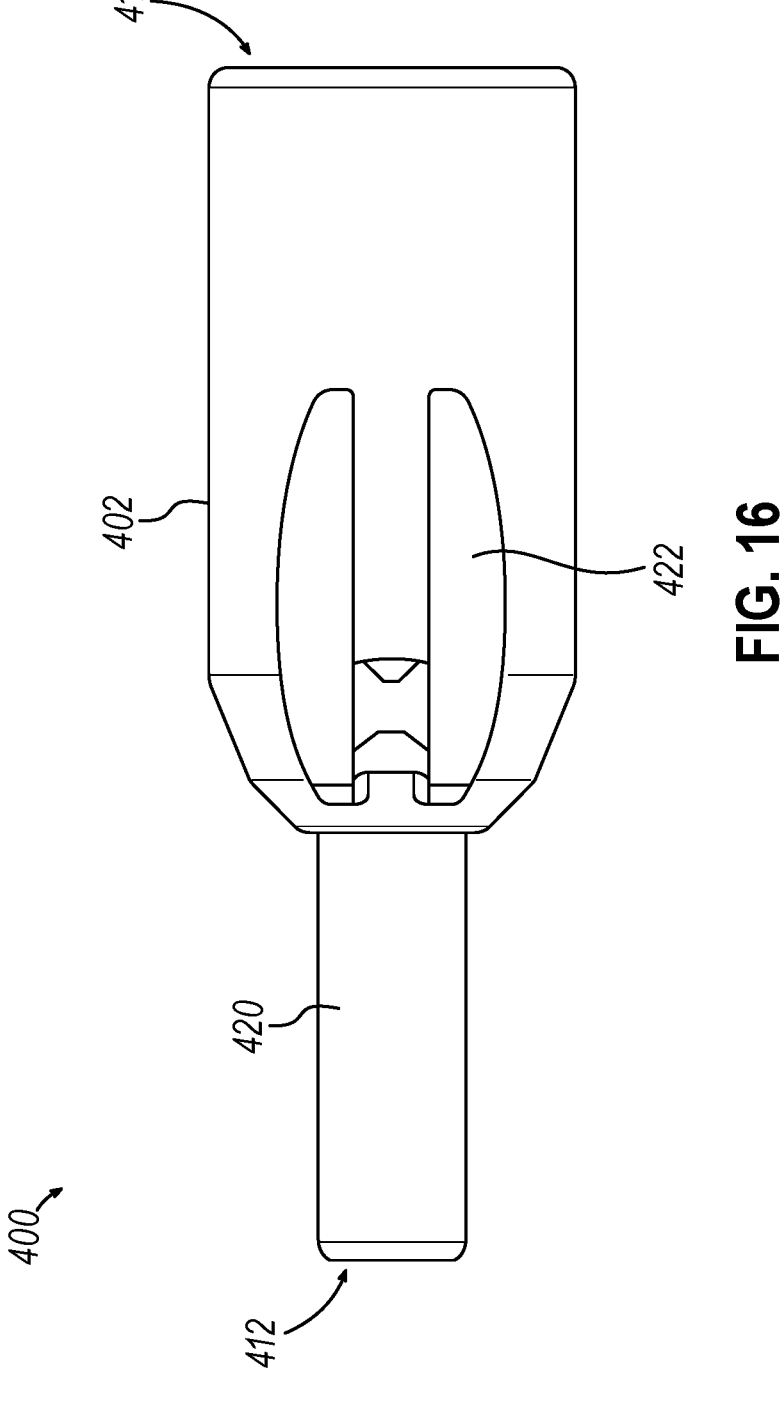
FIG. 16 depicts a top plan view of the navigation adapter of FIG. 14.

FIGS. 14-16 show another example of a form that navigation adapter (120) may take. In particular, FIGS. 14-16 show a navigation adapter (400) that comprises a body (402) having a distal end (412), a proximal end (414), and a bore (418) formed therethrough. Body (402) may be selectively secured to nose portion (104) like body (122) of navigation adapter described above. Body (402) further includes a set of elastomeric features (440) in the form of longitudinally spaced-apart inner annular protrusions that are configured to provide a snug fit with nose portion (104) when navigation adapter (400) is fully seated on nose portion (104), such that body (402) may be secured to nose portion (104) through friction. By way of example only, elastomeric features (440) may comprise rubber o-rings. Alternatively, body (402) may be secured to nose portion (104) in any other suitable fashion.

Body (402) of this example further includes a distally projecting nose portion (420), which has a cylindraceous configuration and is configured extend along a proximal portion of shaft assembly (106) without impeding rotation of shaft assembly (106). One or more position sensors may be contained within nose portion (420). By way of example only, such one or more position sensors may be formed as traces on a flex circuit that is wrapped about the exterior of nose portion (420), positioned in the inner diameter of nose portion (420) or embedded within a wall of nose portion (420). In any of these arrangements, each position sensor of navigation adapter (400) may be configured and operable like position sensor (124) of navigation adapter (120) described above. Each position sensor of navigation adapter (400) has a respective wire (not shown) that may be further coupled with processor (52) via one or more cables (e.g., like cable (126)) or wirelessly. Such wires or cable may be secured to body (402) via a wire retainer (422), which extends transversely from body (402) near the proximal end of nose portion (420).

A slot (430) extends distally from proximal end (414) of body (402) and terminates proximal to distal end (412) of body (402). In particular, slot (430) distally terminates at the proximal end of nose portion (420) in this example. In some versions, slot (430) may provide clearance for the proximal portion of body (402) to flex outwardly as navigation adapter (400) is pressed onto nose portion (104). In some such versions, a resilience of body (402) urges the outwardly flexed portions of body (402) back inwardly, thereby enhancing the grip of body (402) on nose portion (104). A pair of latching features (442) are positioned at the proximal end of slot (430) and are configured to further promote securement of navigation adapter (400) to nose portion (104). In some versions, latching features (442) are omitted.

D. Example of Fourth Variation of Navigation Adapter

Figure 17:
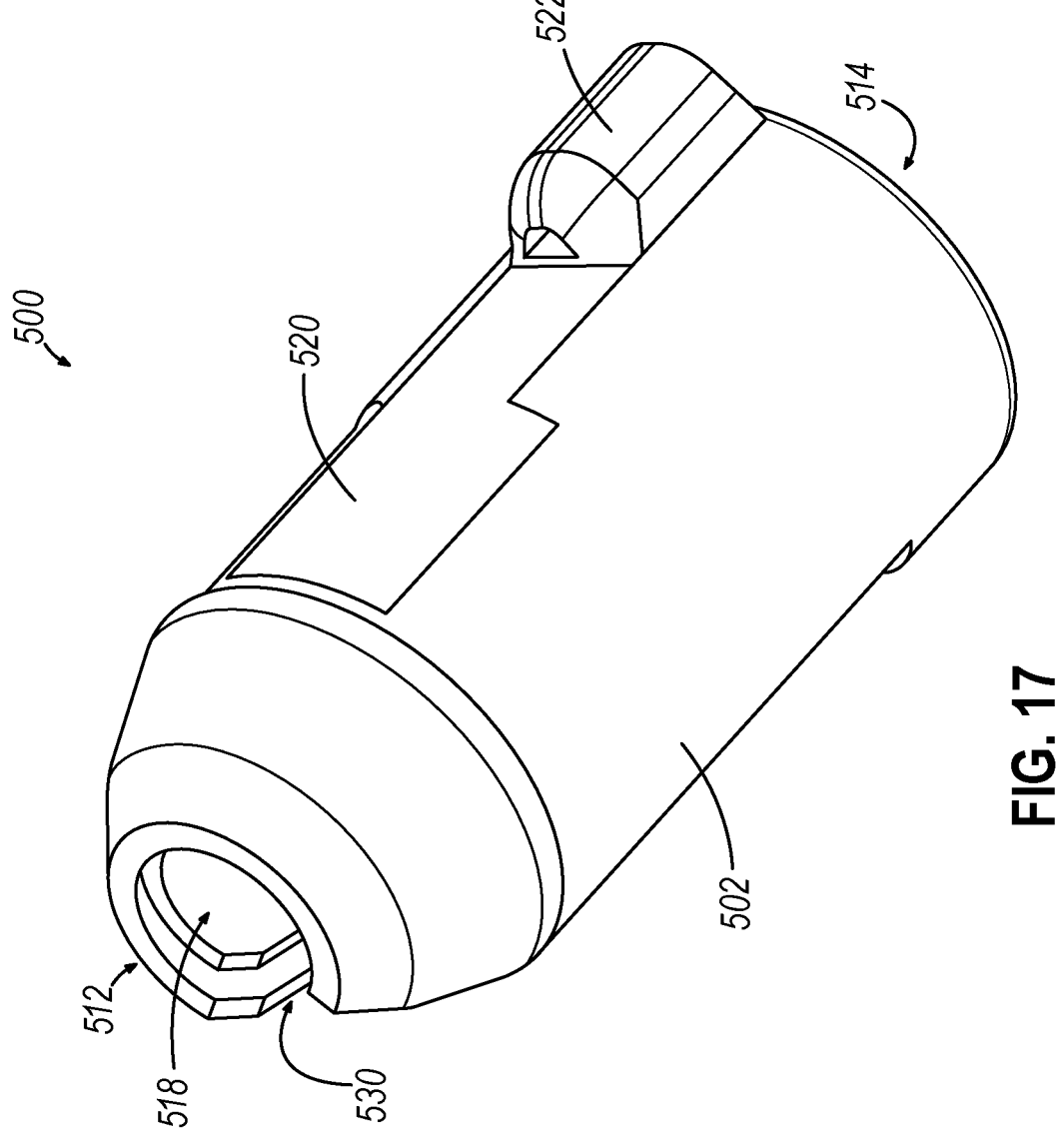
FIG. 17 depicts a perspective view of another example of a navigation adapter that may be secured to the rotary ENT instrument of FIG. 2.
Figure 18:
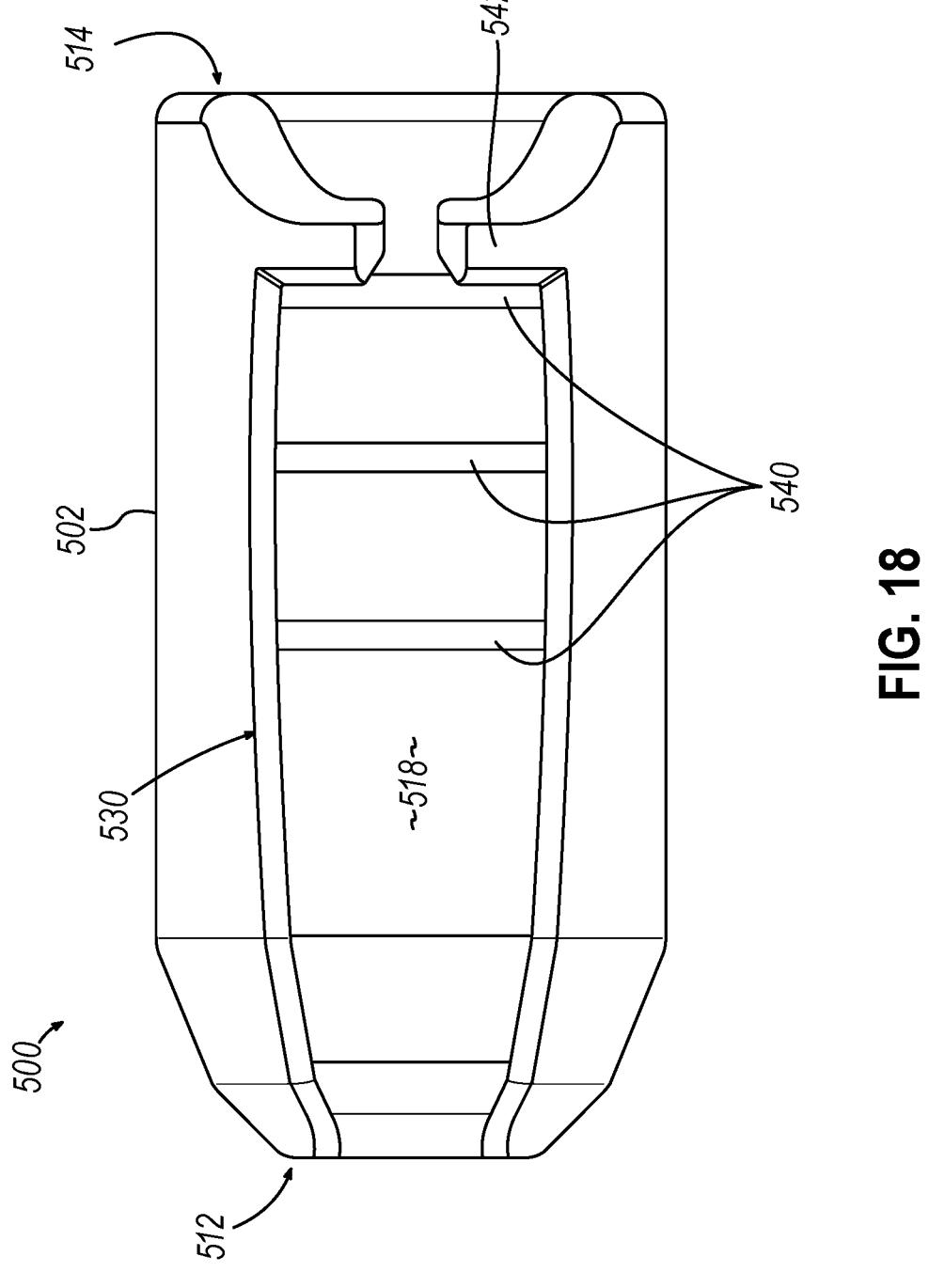
FIG. 18 depicts a bottom plan view of the navigation adapter of FIG. 17.
Figure 19:
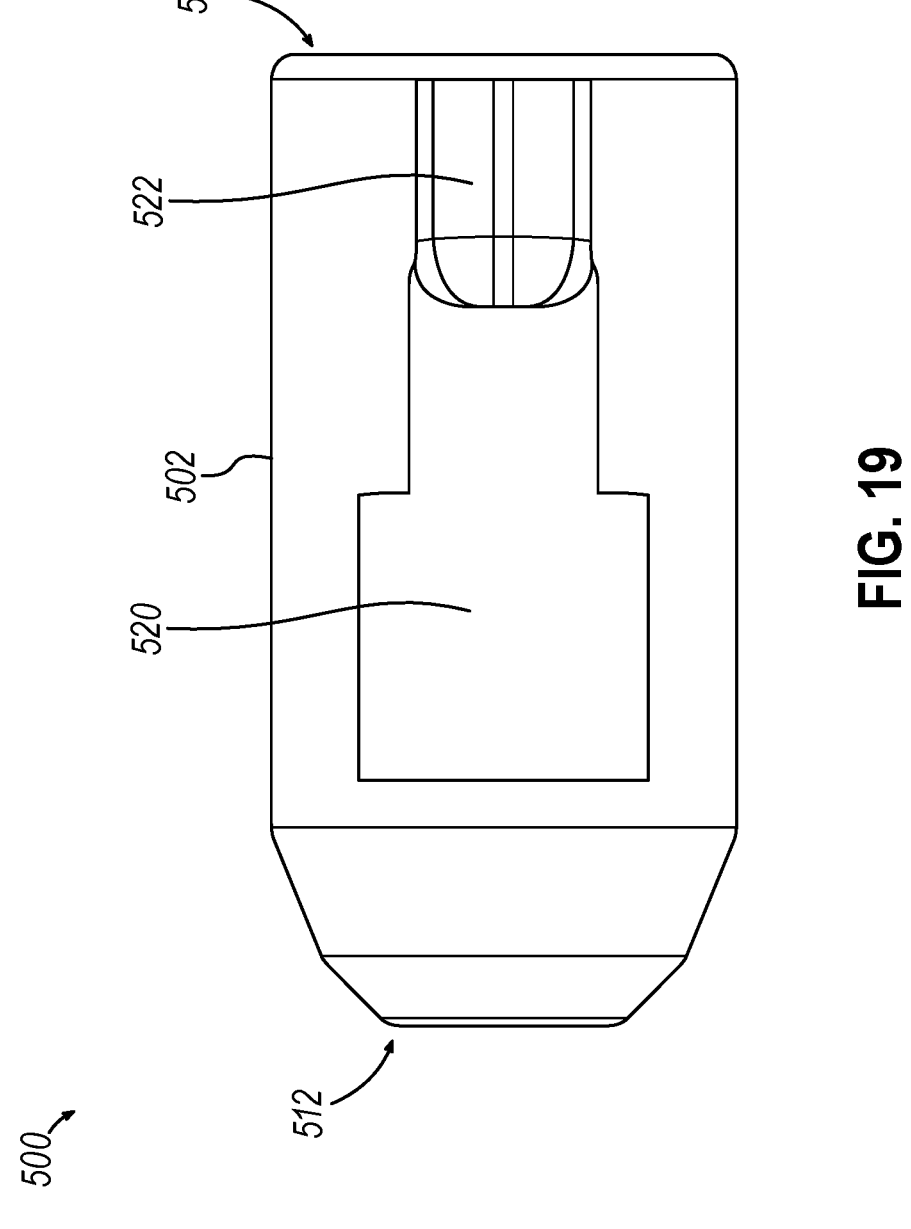
FIG. 19 depicts a top plan view of the navigation adapter of FIG. 18.

FIGS. 17-19 show another example of a form that navigation adapter (120) may take. In particular, FIGS. 17-19 show a navigation adapter (500) that comprises a body (502) having a distal end (512), a proximal end (514), and a bore (518) formed therethrough. Body (502) may be selectively secured to nose portion (104) like body (122) of navigation adapter described above. Body (502) further includes a set of elastomeric features (540) in the form of longitudinally spaced-apart inner annular protrusions that are configured to provide a snug fit with nose portion (104) when navigation adapter (500) is fully seated on nose portion (104), such that body (502) may be secured to nose portion (104) through friction. By way of example only, elastomeric features (540) may comprise rubber o-rings. Alternatively, body (502) may be secured to nose portion (104) in any other suitable fashion.

Body (510) of this example further includes a laterally presented recess (520), which is configured to receive one or more position sensors. By way of example only, such one or more position sensors may be formed as traces on a flex circuit that is positioned within recess (520). A heat shrink wrap, tape, cuff, or other member may be positioned about body (510) to assist in containing the position sensor flex circuit in recess (520). The position sensor(s) of the position sensor flex circuit in recess (520) may be configured and operable like position sensor (124) of navigation adapter (120) described above. A cable (e.g., like cable (126)) may extend from the position sensor flex circuit in recess (520) to couple the position sensor flex circuit with processor (52). This cable may be secured to body (402) via a wire retainer (522), which extends transversely from body (502) near proximal end (514). In some variations, the position sensor flex circuit is coupled with processor (52) wirelessly.

A slot (530) extends distally from proximal end (514) of body (502) and terminates at distal end (512) of body (502).

In some versions, slot (530) may provide clearance for body (502) to flex outwardly as navigation adapter (500) is pressed onto nose portion (104). In some such versions, a resilience of body (502) urges the outwardly flexed portions of body (502) back inwardly, thereby enhancing the grip of body (502) on nose portion (104). A pair of latching features (542) are positioned at the proximal end of slot (530) and are configured to further promote securement of navigation adapter (500) to nose portion (104). In some versions, latching features (542) are omitted.

E. Example of Fifth Variation of Navigation Adapter

Figure 20:
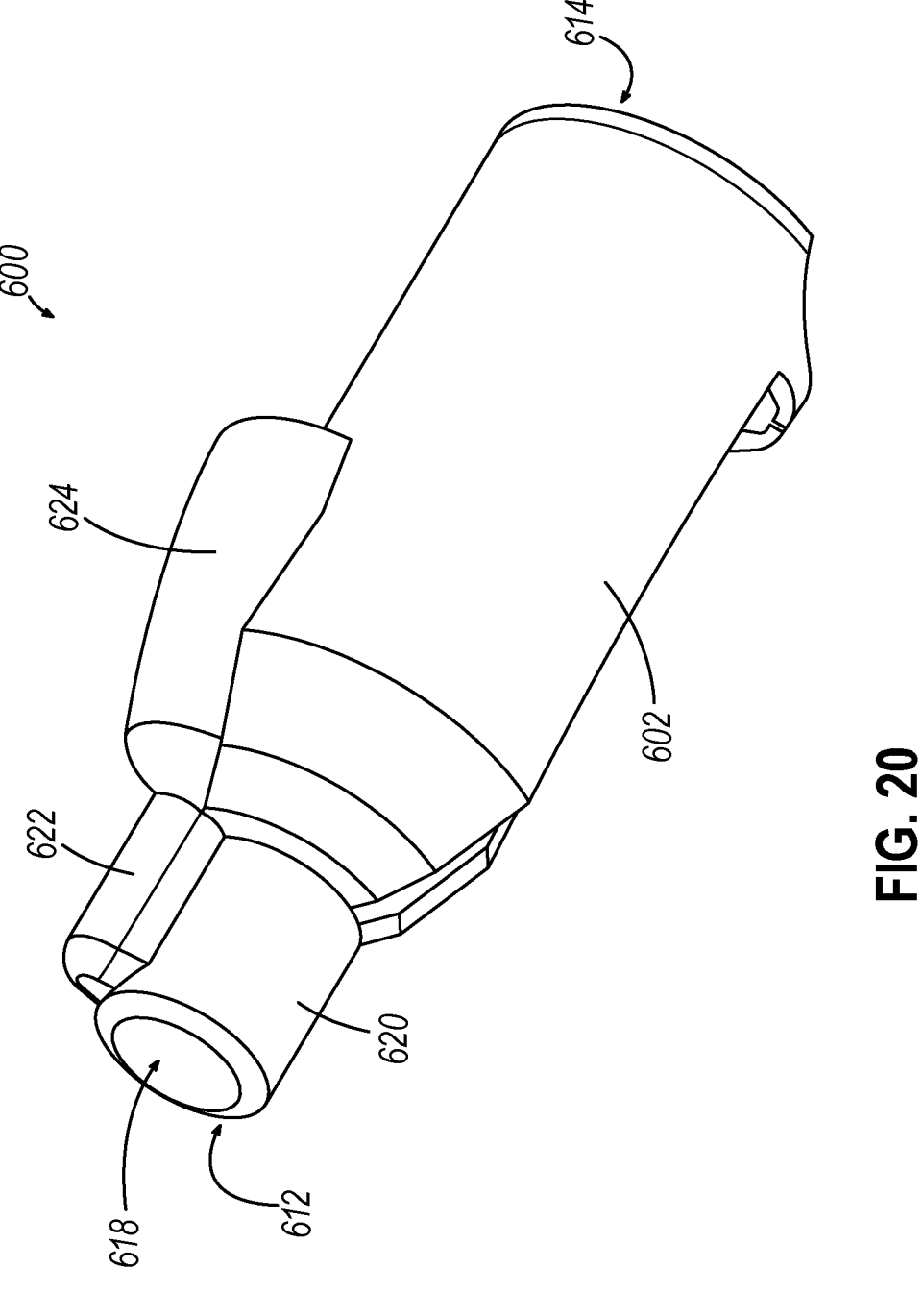
FIG. 20 depicts a perspective view of another example of a navigation adapter that may be secured to the rotary ENT instrument of FIG. 2.
Figure 21:
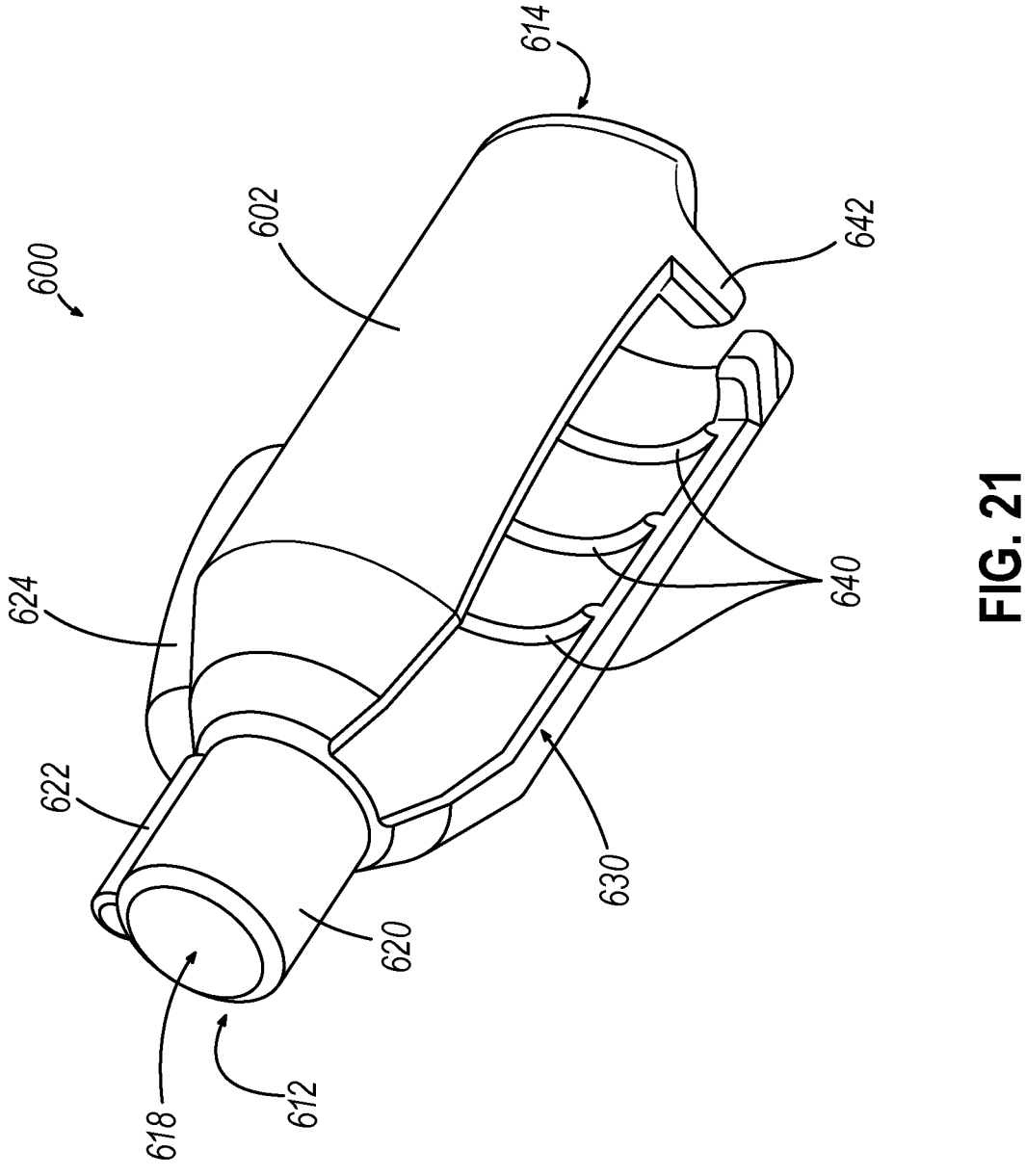
FIG. 21 depicts another perspective view of the navigation adapter of FIG. 20.

FIGS. 20-21 show another example of a form that navigation adapter (120) may take. In particular, FIGS. 20-21 show a navigation adapter (600) that comprises a body (602) having a distal end (612), a proximal end (614), and a bore (618) formed therethrough. Body (602) may be selectively secured to nose portion (104) like body (122) of navigation adapter described above. Body (602) further includes a set of elastomeric features (640) in the form of longitudinally spaced-apart inner annular protrusions that are configured to provide a snug fit with nose portion (104) when navigation adapter (600) is fully seated on nose portion (104), such that body (602) may be secured to nose portion (104) through friction. By way of example only, elastomeric features (640) may comprise rubber o-rings. Alternatively, body (602) may be secured to nose portion (104) in any other suitable fashion.

Body (602) of this example further includes a distally projecting nose portion (620), which has a cylindraceous configuration and is configured extend along a proximal portion of shaft assembly (106) without impeding rotation of shaft assembly (106). A protrusion (622) projects laterally from nose portion (620). A position sensor is contained in protrusion (622). In some versions, the position sensor contained in protrusion (622) comprises a tri-axis sensor. Alternatively, the position sensor contained in protrusion (622) may have any other suitable number of axes. The position sensor contained in protrusion (622) may be configured and operable like position sensor (124) of navigation adapter (120) described above. The position sensor contained in protrusion (622) is further coupled with a wire, which is secured to body (602) via a wire retainer (624). Wire retainer (624) also projects laterally from body (602), just proximal to protrusion (622). The wire in wire retainer (624) may be further coupled with processor (52) via one or more cables (e.g., like cable (126)) or wirelessly.

A slot (630) extends distally from proximal end (614) of body (602) and terminates proximal to distal end (612) of body (602). In particular, slot (630) distally terminates at the proximal end of nose portion (620) in this example. In some versions, slot (630) may provide clearance for the proximal portion of body (602) to flex outwardly as navigation adapter (600) is pressed onto nose portion (104). In some such versions, a resilience of body (602) urges the outwardly flexed portions of body (602) back inwardly, thereby enhancing the grip of body (602) on nose portion (104). A pair of latching features (642) are positioned at the proximal end of slot (630) and are configured to further promote securement of navigation adapter (600) to nose portion (104). In some versions, latching features (642) are omitted.

F. Example of Sixth Variation of Navigation Adapter

Figure 22:
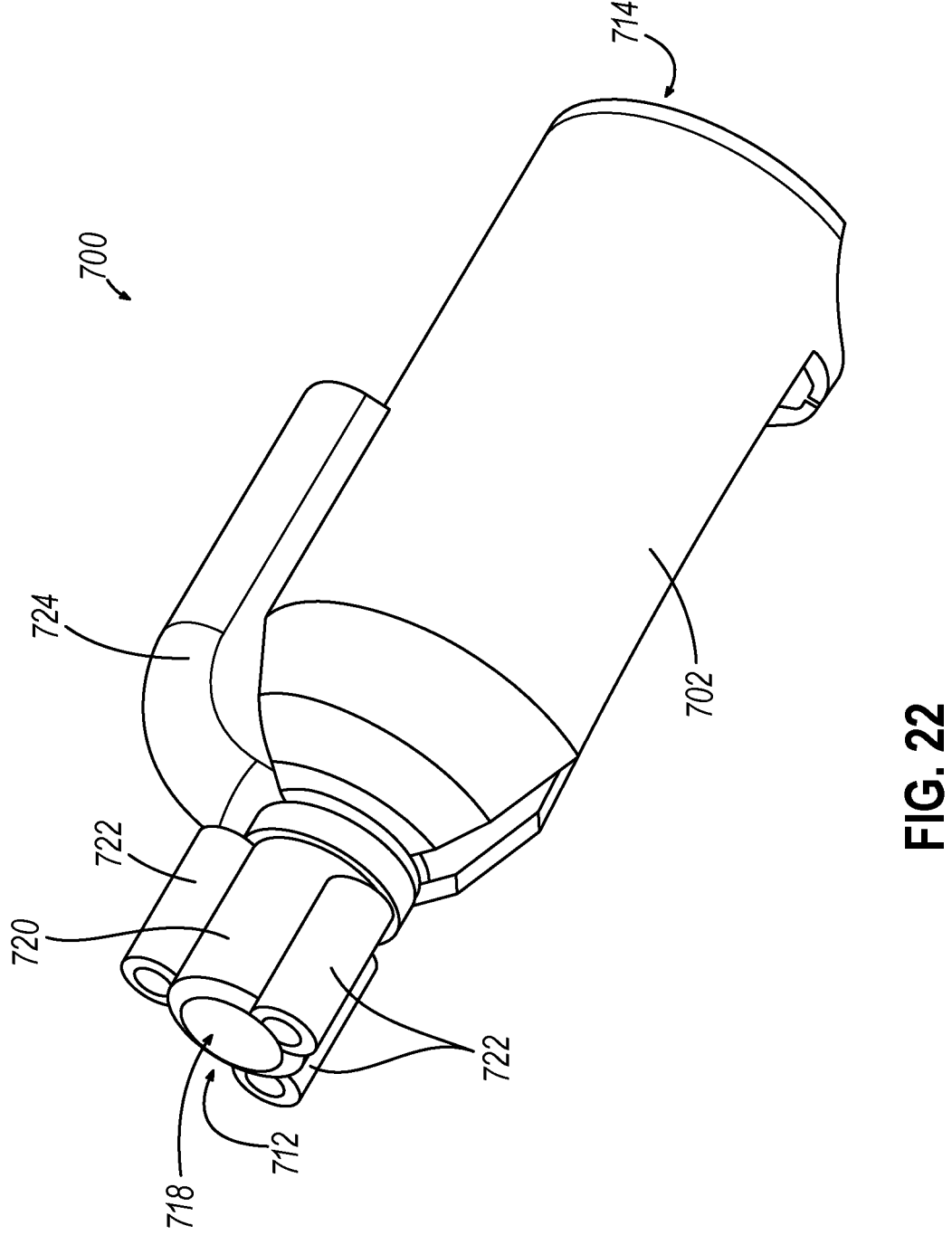
FIG. 22 depicts a perspective view of another example of a navigation adapter that may be secured to the rotary ENT instrument of FIG. 2.
Figure 23:
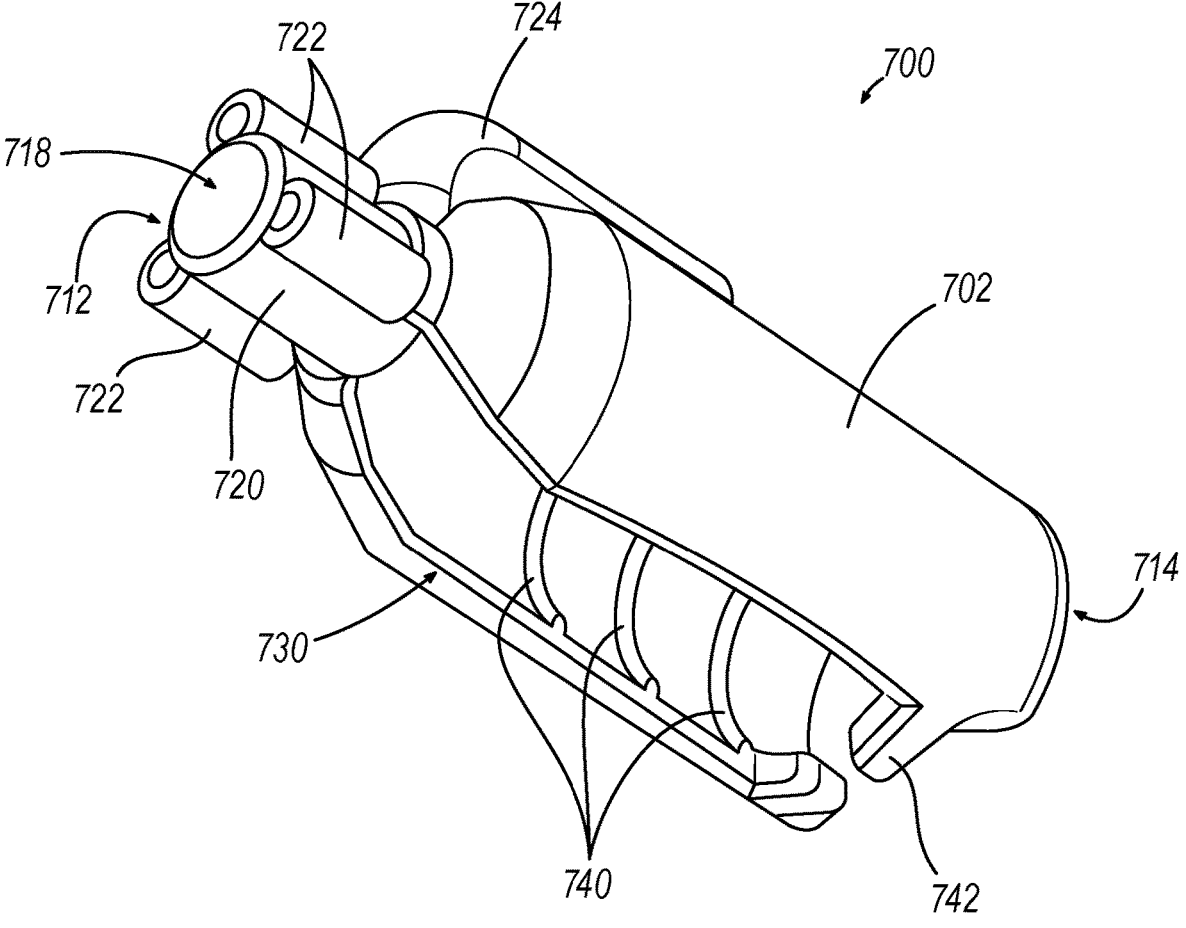
FIG. 23 depicts another perspective view of the navigation adapter of FIG. 22.

FIGS. 22-23 show another example of a form that navigation adapter (120) may take. In particular, FIGS. 22-23 show a navigation adapter (700) that comprises a body (702) having a distal end (712), a proximal end (714), and a bore (718) formed therethrough. Body (702) may be selectively secured to nose portion (104) like body (122) of navigation adapter described above. Body (702) further includes a set of elastomeric features (740) in the form of longitudinally spaced-apart inner annular protrusions that are configured to provide a snug fit with nose portion (104) when navigation adapter (700) is fully seated on nose portion (104), such that body (710) may be secured to nose portion (104) through friction. By way of example only, elastomeric features (740) may comprise rubber o-rings. Alternatively, body (702) may be secured to nose portion (104) in any other suitable fashion.

Body (702) of this example further includes a distally projecting nose portion (720), which has a cylindraceous configuration and is configured extend along a proximal portion of shaft assembly (106) without impeding rotation of shaft assembly (106). Three protrusions (722) project laterally from nose portion (720). In the present example, protrusions (722) are angularly spaced apart from each other equidistantly about a central longitudinal axis of bore (718), though protrusions (722) may alternatively be spaced in any other suitable arrangement. A position sensor is contained in each protrusion (722). In some versions, the position sensor contained in each protrusion (722) comprises a tri-axis sensor, such that navigation adapter (700) contains a total of three tri-axis sensors. Alternatively, the position sensor contained in each protrusion (722) may have any other suitable number of axes. The position sensor contained in each protrusion (722) may be configured and operable like position sensor (124) of navigation adapter (120) described above. The position sensor contained in each protrusion (722) is further coupled with a respective wire. These wires are secured to body (702) via a wire retainer (724). Wire retainer (724) also projects laterally from body (702), just proximal to protrusions (722). The wires in wire retainer (724) may be further coupled with processor (52) via one or more cables (e.g., like cable (126)) or wirelessly.

A slot (730) extends distally from proximal end (714) of body (702) and terminates proximal to distal end (712) of body (702). In particular, slot (730) distally terminates at the proximal end of nose portion (720) in this example. In some versions, slot (730) may provide clearance for the proximal portion of body (702) to flex outwardly as navigation adapter (700) is pressed onto nose portion (104). In some such versions, a resilience of body (702) urges the outwardly flexed portions of body (702) back inwardly, thereby enhancing the grip of body (702) on nose portion (104). A pair of latching features (742) are positioned at the proximal end of slot (730) and are configured to further promote securement of navigation adapter (700) to nose portion (104). In some versions, latching features (742) are omitted.

IV. Example of Jig for Calibrating ENT Instrument Equipped with Navigation Adapter As noted above, when a navigation adapter (120, 200, 400, 500, 600, 700, 800) is secured to an instrument (100), the distance between position sensor (124) and end effector (108) may be fixed during operation of instrument (100). To the extent that this fixed distance is "known" by processor (52), processor (52) may readily determine the real-time position of end effector (108) within a three-dimensional space (i.e., within the head (H) of the patient (P), etc.) based on the position-indicative signals from position sensor (124). However, in some instances, it may be necessary to "teach" this fixed distance to processor (52). To that end, it may be beneficial to calibrate IGS system (50) with respect to an instrument (100) that is fitted with a navigation adapter (120, 200, 400, 500, 600, 700, 800). Such a calibration process may include the use of a jig.

Figure 24:
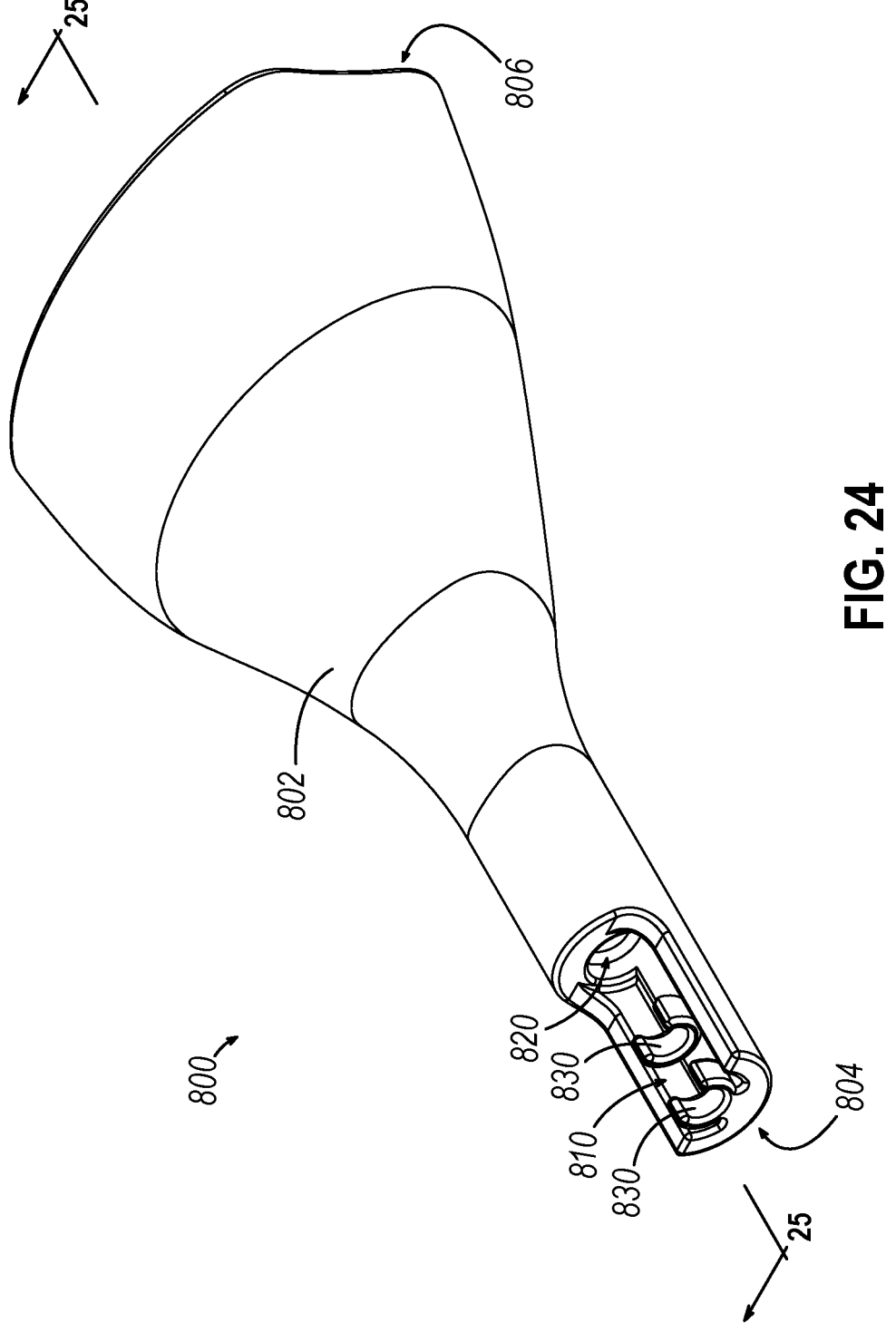
FIG. 24 depicts a perspective view of an example of a jig that may be used when calibrating a navigation adapter with the rotary ENT instrument of FIG. 2.
Figure 25:
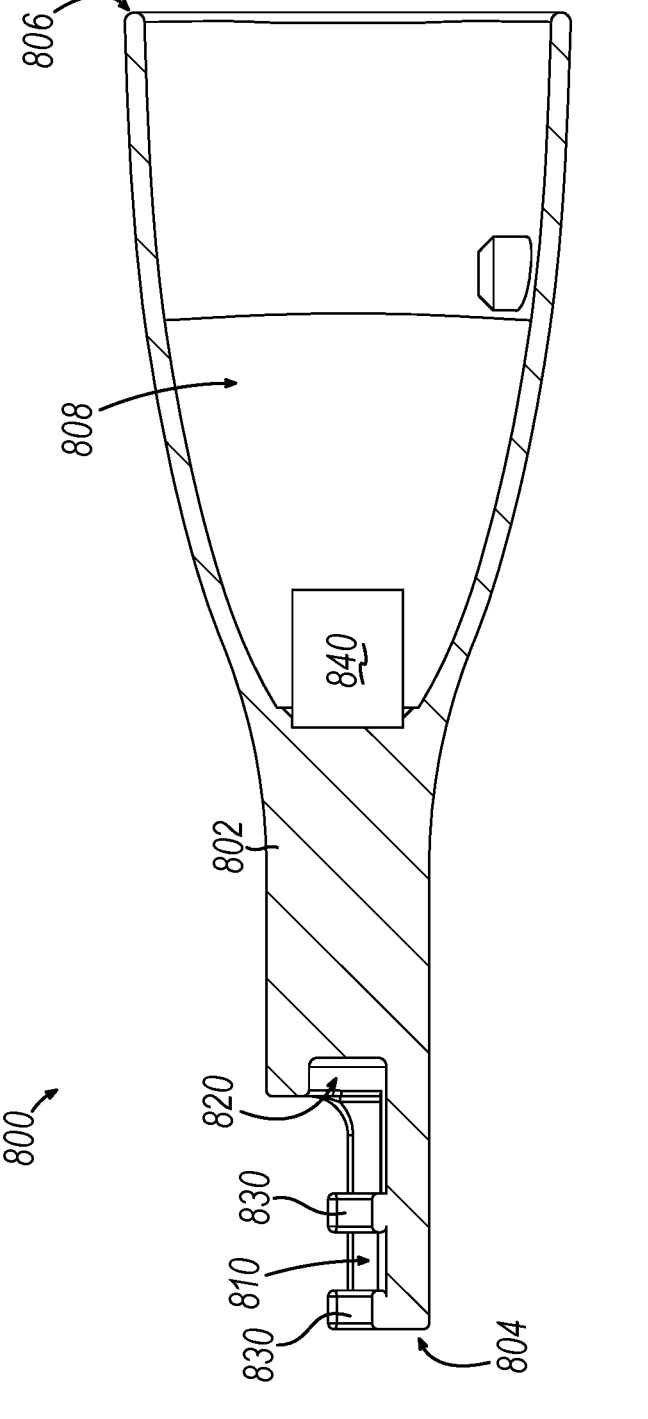
FIG. 25 depicts a cross-sectional side view of the jig of FIG. 24, taken along line 25-25 of FIG. 24.

FIGS. 24-25 show an example of a form that such a calibration jig may take. In particular, FIGS. 24-25 show an example of a jig (800) that includes a body (802) having a distal end (804) and a proximal end (806). A laterally facing recess (810) is formed near distal end (804). A distally facing recess (820) is positioned at a proximal end of recess (810). A pair of latch features (830) are located in recess (810). In other variations, more or fewer than two latch features (830) are located in recess (810).

As shown in FIG. 25, body (802) further defines a proximally facing recess (808). A calibration position sensor (840) is fixedly secured in recess (808). Alternatively, calibration position sensor (840) may be fixedly secured anywhere else in or on body (802). Calibration position sensor (840) may comprise one or more coils. When such a coil is positioned within an alternating electromagnetic field generated by field generators (64), the alternating magnetic field may generate electrical current in the coil, and this electrical current may be communicated via wire or wirelessly to processor (52). This phenomenon may enable IGS navigation system (50) to determine the real-time position of calibration position sensor (840) within a three-dimensional space. Since calibration position sensor (840) is fixedly secured relative to body (802), the distance between calibration position sensor (840) and the proximal end of recess (820) is fixed. This fixed distance may be "known" by processor (52) in advance of the calibration process.

Recesses (810, 820) are configured to receive end effector (108) and a distal portion of shaft assembly (106). In particular, after securing navigation adapter (120, 200, 400, 500, 600, 700, 800) to instrument (100), an operator may insert end effector (108) into recess (820) until end effector (108) contacts the proximal end of recess (820). The operator may then secure instrument (100) relative to jig by engaging the distal portion of shaft assembly (106) with latch features (830). In some versions, latch features (830) are configured to resiliently deflect and latch onto the distal portion of shaft assembly (106) to thereby firmly secure jig (800) relative to instrument (100). Alternatively, jig (800) may be removably yet firmly secured to instrument (100) using any other suitable structures or techniques.

Once navigation adapter (120, 200, 400, 500, 600, 700, 800) has been secured to instrument (100) and jig (800) has also been secured to instrument (100), the operator may activate an electromagnetic field around instrument (100) and jig (800). This may cause position sensor (124) of navigation adapter (120, 200, 400, 500, 600, 700, 800) and calibration position sensor (840) to simultaneously generate signals indicating the respective real-time positions of position sensor (124) of navigation adapter (120, 200, 400, 500, 600, 700, 800) and calibration position sensor (840) in three-dimensional space. With processor (52) "knowing" the respective real-time positions of position sensor (124) of navigation adapter (120, 200, 400, 500, 600, 700, 800) and calibration position sensor (840) in three-dimensional space based on the generated signals, and with processor already "knowing" the fixed distance between calibration position sensor (840) and the proximal face of recess (820), processor (52) may determine the distance between position sensor (124) of navigation adapter (120, 200, 400, 500, 600, 700, 800) and end effector (108) since end effector (108) is seated against the proximal face of recess (820). Processor (52)

may thus "learn" the distance between position sensor (124) of navigation adapter (120, 200, 400, 500, 600, 700, 800) and end effector (108) through the calibration process outlined above. With this calibrated "knowledge" of the distance between position sensor (124) of navigation adapter (120, 200, 400, 500, 600, 700, 800) and end effector (108), processor (52) may subsequently determine the real-time position of end effector (108) within a three-dimensional space (i.e., within the head (H) of the patient (P), etc.) based on the position-indicative signals from position sensor (124) as described above.

V. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body defining a bore, the bore being sized to receive a portion of a medical instrument having a rotary member, the rotary member being configured to rotate about a longitudinal axis, the rotary member being further configured generate interference in an electromagnetic field while rotating about the longitudinal axis, the body further being configured to be fixedly secured to the medical instrument while allowing rotation of the rotary member about the longitudinal axis; and (b) a first position sensor supported by the body, the first position sensor being configured to generate a signal indicating a position of the first position sensor in three-dimensional space, the first position sensor being oriented to offset the interference generated by the rotary member.

Example 2

The apparatus of Example 1, the interference being oriented along a first axis, the first position sensor being oriented along a second axis, the second axis being perpendicular to the first axis.

Example 3

The apparatus of any of Examples 1 through 2, the bore being positioned to align with the longitudinal axis when the body is fixedly secured to the medical instrument.

Example 4

The apparatus of any of Examples 1 through 3, the first position sensor being positioned to be laterally offset relative to the longitudinal axis when the body is fixedly secured to the medical instrument.

Example 5

The apparatus of any of Examples 1 through 4, the body having a proximal portion and a distal portion, the first position sensor being located at the distal portion.

Example 6

The apparatus of any of Examples 1 through 5, further comprising a conductor coupled with the first position sensor, the conductor being configured to conduct electrical signals from the first position sensor.

Example 7

The apparatus of Example 6, the body including a passageway, the conductor being disposed in the passageway.

Example 8

The apparatus of Example 7, the passageway being offset from the bore.

Example 9

The apparatus of any of Examples 6 through 8, the body further including a laterally projecting protrusion, at least a portion of the conductor being disposed in the protrusion.

Example 10

The apparatus of any of Examples 6 through 9, the body further including a retainer, at least a portion of the conductor being secured relative to the body via the retainer.

Example 11

The apparatus of any of Examples 6 through 10, the conductor comprising a wire.

Example 12

The apparatus of any of Examples 1 through 11, at least a portion of the body being deformable.

Example 13

The apparatus of Example 12, the body further defining a slot, the slot being configured to accommodate deformation of the body.

Example 14

The apparatus of any of Examples 1 through 13, the body being configured to be fixedly secured to a nose portion of the medical instrument, the nose portion of the medical instrument being positioned between the rotary member and a body of the medical instrument.

Example 15

The apparatus of any of Examples 1 through 14, the body being configured to be fixedly secured to the medical instrument through friction.

Example 16

The apparatus of Example 15, the body further including one or more elastomeric features configured to engage the medical instrument to thereby provide friction with the medical instrument.

Example 17

The apparatus of Example 16, the one or more elastomeric features being positioned within the bore.

Example 18

The apparatus of any of Examples 1 through 17, the first position sensor comprising a single-axis coil sensor.

Example 19

The apparatus of any of Examples 1 through 17, the first position sensor comprising a dual-axis coil sensor.

Example 20

The apparatus of any of Examples 1 through 17, the first position sensor comprising a tri-axis coil sensor.

Example 21

The apparatus of any of Examples 1 through 20, further comprising a second position sensor supported by the body, the second position sensor being configured to generate a signal indicating a position of the second position sensor in three-dimensional space, the second position sensor being oriented to offset the interference generated by the rotary member.

Example 22

The apparatus of Example 21, the second position sensor being positioned to be angularly spaced away from the first position sensor about the longitudinal axis when the body is fixedly secured to the medical instrument.

Example 23

The apparatus of any of Examples 21 through 22, further comprising a third position sensor supported by the body, the third position sensor being configured to generate a signal indicating a position of the third position sensor in three-dimensional space, the third position sensor being oriented to offset the interference generated by the rotary member.

Example 24

The apparatus of Example 23, the third position sensor being positioned to be angularly spaced away from the first and second position sensors about the longitudinal axis when the body is fixedly secured to the medical instrument.

Example 25

The apparatus of Example 24, the third position sensor being positioned to be angularly spaced away from the second position sensors by about 90 degrees about the longitudinal axis when the body is fixedly secured to the medical instrument.

Example 26

The apparatus of any of Examples 24 through 25, the second position sensor being positioned to be angularly spaced away from the first position sensors by about 90 degrees about the longitudinal axis when the body is fixedly secured to the medical instrument.

Example 27

The apparatus of any of Examples 24 through 25, the third position sensor being positioned to be angularly spaced away from the first position sensors by about 180 degrees about the longitudinal axis when the body is fixedly secured to the medical instrument.

Example 28

The apparatus of Example 24, the first, second, and third positions sensors being positioned to be angularly spaced away from each other by about 120 degrees about the longitudinal axis when the body is fixedly secured to the medical instrument.

Example 29

The apparatus of any of Examples 1 through 28, the body defining a laterally projecting protrusion, the first position sensor being contained in the laterally projecting protrusion.

Example 30

The apparatus of any of Examples 1 through 29, the body defining a recess, the first position sensor being contained in the recess.

Example 31

The apparatus of any of Examples 1 through 30, the first position sensor comprising at least one coil formed by one or more traces on a flex circuit substrate.

Example 32

The apparatus of any of Examples 1 through 31, the body including a nose portion, the first position sensor being positioned on the nose portion.

Example 33

The apparatus of Example 32, the nose portion being configured to be positioned over a shaft assembly of the medical instrument when the body is fixedly secured to the medical instrument.

Example 34

An apparatus, comprising: (a) a medical instrument, the medical instrument comprising: (i) an instrument body, (ii)

a shaft assembly extending distally from the instrument body, and (iii) an end effector at a distal end of the shaft assembly, the shaft assembly being operable to drive rotation of the end effector about a longitudinal axis, the medical instrument being configured to generate interference in an electromagnetic field while the end effector rotates about the longitudinal axis; and (b) a navigation adapter, the navigation adapter comprising: (i) an adapter body defining a bore, the bore being sized to receive a portion of the medical instrument, the adapter body further being configured to be fixedly secured to the medical instrument while allowing rotation of the end effector about the longitudinal axis, and (ii) a first position sensor supported by the adapter body, the first position sensor being configured to generate a signal indicating a position of the first position sensor in three-dimensional space, the first position sensor being oriented to offset the interference generated by the medical instrument.

Example 35

The apparatus of Example 34, the end effector comprising a bur.

Example 36

The apparatus of Example 34, the end effector comprising a drill bit.

Example 37

The apparatus of Example 34, the end effector comprising a shaver head.

Example 38

The apparatus of any of Examples 34 through 37, the medical instrument being operable to drive rotation of the end effector at an angular velocity of at least about 80,000 revolutions per minute.

Example 39

The apparatus of any of Examples 34 through 38, the instrument body having a distal nose portion.

Example 40

The apparatus of Example 39, the adapter body being configured to be fixedly secured to the distal nose portion.

Example 41

The apparatus of any of Examples 34 through 40, the adapter body having a distally projecting nose portion.

Example 42

The apparatus of Example 41, the distally projecting nose portion being configured to extend along a portion of the shaft assembly when the adapter body is fixedly secured to the medical instrument.

Example 43

The apparatus of any of Examples 34 through 42, further comprising a field generator assembly, the field generator assembly being configured to generate an electromagnetic field, the first position sensor being configured to generate a signal indicating a position of the first position sensor in three-dimensional space in response to an electromagnetic field generated by the field generator assembly.

Example 44

An apparatus, comprising: (a) a body, the body including: (i) a laterally presented recess, the laterally presented recess being configured to receive a distal portion of a shaft assembly of a medical instrument, (ii) a distally presented recess adjacent to the laterally presented recess, the distally presented recess having a proximal engagement surface, the distally presented recess being configured to receive an end effector of the medical instrument, the end effector being disposed at a distal end of the shaft assembly, the proximal engagement surface being configured to engage a distal end of the end effector, and (iii) a latch, the latch being configured to retain the shaft assembly and the end effector relative to the body; and (b) a position sensor, the position sensor being secured relative to the body at a fixed distance from the proximal engagement surface, the position sensor being configured to generate a signal indicating a position of the position sensor in three-dimensional space.

Example 45

The apparatus of Example 44, the latch being positioned at the laterally presented recess.

VI. Miscellaneous

It should be understood that any of the teachings, expressions, embodiments, examples, etc. described herein may be combined with any of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination.

Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body defining a bore, the bore being sized to receive a portion of a medical instrument having a rotary member, the rotary member being configured to rotate about a longitudinal axis, the rotary member being further configured generate interference in an electromagnetic field while rotating about the longitudinal axis, the body further being configured to be fixedly secured to the medical instrument while allowing rotation of the rotary member about the longitudinal axis; and
   (b) a first position sensor supported by the body, the first position sensor being configured to generate a signal indicating a position of the first position sensor in three-dimensional space, the first position sensor being oriented to offset the interference generated by the rotary member.

2. The apparatus of claim 1, the interference being oriented along a first axis, the first position sensor being oriented along a second axis, the second axis being perpendicular to the first axis.

3. The apparatus of claim 1, the bore being positioned to align with the longitudinal axis when the body is fixedly secured to the medical instrument.

4. The apparatus of claim 1, the first position sensor being positioned to be laterally offset relative to the longitudinal axis when the body is fixedly secured to the medical instrument.

5. The apparatus of claim 1, the body having a proximal portion and a distal portion, the first position sensor being located at the distal portion.

6. The apparatus of claim 1, further comprising a conductor coupled with the first position sensor, the conductor being configured to conduct electrical signals from the first position sensor.

7. The apparatus of claim 1, at least a portion of the body being deformable.

8. The apparatus of claim 1, the body being configured to be fixedly secured to a nose portion of the medical instrument, the nose portion of the medical instrument being positioned between the rotary member and a body of the medical instrument.

9. The apparatus of claim 1, the body being configured to be fixedly secured to the medical instrument through friction.

10. The apparatus of claim 1, the first position sensor comprising a single-axis coil sensor.

11. The apparatus of claim 1, the first position sensor comprising a dual-axis coil sensor.

12. The apparatus of claim 1, the first position sensor comprising a tri-axis coil sensor.

13. The apparatus of claim 1, further comprising a second position sensor supported by the body, the second position sensor being configured to generate a signal indicating a position of the second position sensor in three-dimensional space, the second position sensor being oriented to offset the interference generated by the rotary member.

14. The apparatus of claim 1, the body defining a laterally projecting protrusion, the first position sensor being contained in the laterally projecting protrusion.

15. The apparatus of claim 1, the body defining a recess, the first position sensor being contained in the recess.

16. The apparatus of claim 1, the first position sensor comprising at least one coil formed by one or more traces on a flex circuit substrate.

17. The apparatus of claim 1, the body including a nose portion, the first position sensor being positioned on the nose portion.

18. The apparatus of claim 17, the nose portion being configured to be positioned over a shaft assembly of the medical instrument when the body is fixedly secured to the medical instrument.

19. An apparatus, comprising:
   (a) a medical instrument, the medical instrument comprising:
      (i) an instrument body,
      (ii) a shaft assembly extending distally from the instrument body, and
      (iii) an end effector at a distal end of the shaft assembly, the shaft assembly being operable to drive rotation of the end effector about a longitudinal axis, the medical instrument being configured to generate interference in an electromagnetic field while the end effector rotates about the longitudinal axis; and
   (b) a navigation adapter, the navigation adapter comprising:
      (i) an adapter body defining a bore, the bore being sized to receive a portion of the medical instrument, the adapter body further being configured to be fixedly secured to the medical instrument while allowing rotation of the end effector about the longitudinal axis, and
      (ii) a first position sensor supported by the adapter body, the first position sensor being configured to generate a signal indicating a position of the first position sensor in three-dimensional space, the first position sensor being oriented to offset the interference generated by the medical instrument.

20. An apparatus, comprising:

(a) a body, the body including:

(i) a laterally presented recess, the laterally presented recess being configured to receive a distal portion of a shaft assembly of a medical instrument,

(ii) a distally presented recess adjacent to the laterally presented recess, the distally presented recess having a proximal engagement surface, the distally presented recess being configured to receive an end effector of the medical instrument, the end effector being disposed at a distal end of the shaft assembly, the proximal engagement surface being configured to engage a distal end of the end effector, and (iii) a latch, the latch being configured to retain the shaft assembly and the end effector relative to the body; and (b) a position sensor, the position sensor being secured relative to the body at a fixed distance from the proximal engagement surface, the position sensor being configured to generate a signal indicating a position of the position sensor in three-dimensional space.

\* \* \* \* \*